US012679837B2

(12) United States Patent
Zhou et al.

(10) Patent No.: US 12,679,837 B2
(45) Date of Patent: Jul. 14, 2026

(54) AMINOPYRIMIDINE COMPOUND AS CDK2/4/6 TRIPLE INHIBITOR

(71) Applicant: CISEN PHARMACEUTICAL CO., LTD, Jining (CN)

(72) Inventors: Ming Zhou, Shanghai (CN); Zhaobing Xu, Shanghai (CN); Gang Li, Shanghai (CN); Lihong Hu, Shanghai (CN); Charles Z. Ding, Shanghai (CN); Wen Jiang, Shanghai (CN); Guoping Hu, Shanghai (CN); Jian Li, Shanghai (CN); Shuhui Chen, Shanghai (CN)

(73) Assignee: CISEN PHARMACEUTICAL CO., LTD, Jining (CN)

( * ) Notice: Subject to any disclaimer, the term of this patent is extended or adjusted under 35 U.S.C. 154(b) by 1003 days.

(21) Appl. No.: 17/769,385

(22) PCT Filed: Oct. 16, 2020

(86) PCT No.: PCT/CN2020/121390
§ 371 (c)(1),
(2) Date: Apr. 15, 2022

(87) PCT Pub. No.: WO2021/073593
PCT Pub. Date: Apr. 22, 2021

(65) Prior Publication Data

US 2024/0190861 A1 Jun. 13, 2024

(30) Foreign Application Priority Data

Oct. 17, 2019 (CN) ......................... 201910988432.0
Jun. 18, 2020 (CN) ......................... 202010558823.1

(51) Int. Cl.
*C07D 471/04* (2006.01)
*A61K 31/519* (2006.01)
*A61P 35/00* (2006.01)
*C07D 471/10* (2006.01)
*C07D 487/04* (2006.01)
*C07D 487/10* (2006.01)

(52) U.S. Cl.
CPC .......... *C07D 471/04* (2013.01); *A61K 31/519* (2013.01); *A61P 35/00* (2018.01); *C07D 471/10* (2013.01); *C07D 487/04* (2013.01); *C07D 487/10* (2013.01)

(58) Field of Classification Search
CPC .. C07D 471/04; C07D 471/10; C07D 487/04; C07D 487/10; A61K 31/519; A61P 35/00
See application file for complete search history.

(56) References Cited

U.S. PATENT DOCUMENTS

2009/0318441 A1 12/2009 Brain et al.
2019/0135817 A1 5/2019 Behenna et al.
2020/0115378 A1* 4/2020 Sokolsky ............. C07D 471/04

FOREIGN PATENT DOCUMENTS

CN 101594871 A 12/2009
EA 201990196 A1 7/2019
WO WO-2020168178 A1 8/2020
WO WO-2020168197 A1 * 8/2020 .............. A61P 25/00

OTHER PUBLICATIONS

Berge Journal of Pharmaceutical Sciences 1977 (Year: 1977).*
Mar. 24, 2023 First Office Action issued in Chinese Patent Application No. 2020800728135.
Oct. 25, 2023 Supplementary European Search Report issued in European Patent Application No. 20877068.5.
Dec. 30, 2020 International Search Report issued in International Patent Application No. PCT/CN2020/121390.
Dec. 30, 2020 Written Opinion of the International Searching Authority issued in International Patent Application No. PCT/CN2020/121390.
Asghar et al. The history and future of targeting cyclin-dependent kinases in cancer therapy, Nat. Rev. Drug. Discov.2015;14(2):130-146.
Nakayama et al., Gene amplification CCNE1 is related to poor survival and potential therapeutic target in ovarian cancer, cancer (2010).
Etemadmoghadam et al., Resistance to CDK2 inhibitors is associated with selection of polyploidy cells in CCNE1-Amplified Ovarian cancer, clin cancer res (2013)19:5960-71.
Au-Yeung et al., selective targeting of cyclin E1-Amplified high-grade serous ovarian cancer by cyclin-dependent kinase 2 and AKT inhibition, Clin. Cancer res.(2017) 30:297-303.
Ooi et al., Gene amplification of CCNE1, CCND1, and CDK6 in gastric cancers detected by multiplex ligation-dependent probe amplification and fluorescence in situ hybridization, Hum Pathol. (2017) 61: 58-67.
Noske et al., detection of CCNE1/UR/(19q12) amplification by in situ hybridization is common in high grade and type 2 endometrial cancer, oncotarget (2017) 8:14794-14805.

(Continued)

*Primary Examiner* — Samantha L Shterengarts
(74) *Attorney, Agent, or Firm* — Harness, Dickey & Pierce, P.L.C.

(57) ABSTRACT

Disclosed is an aminopyrimidine compound as a CDK2/4/6 inhibitor, and specifically disclosed are the compound represented by formula (I) and a pharmaceutically acceptable salt thereof, and an application of the compound represented by formula (I) and the pharmaceutically acceptable salt thereof in the preparation of a medicament for treating solid tumor.

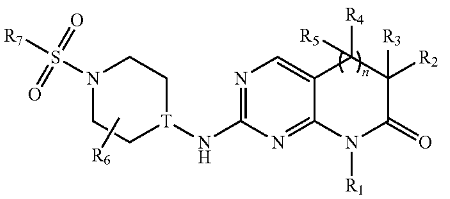

16 Claims, No Drawings

(56) References Cited

OTHER PUBLICATIONS

Caldon et al., Cyclin E2 overexpression is associated with endocrine resistance but not insensitivity to CDK2 inhibition in human breast cancer cells. Mol cancer Ther. (2012) 11:1488-99.

Herrera-abreu et al., Early adaption and acquired resistance to CDK4/6 inhibition in Estrogen Receptor-positive breast cancer, cancer res.(2016) 76:2301-2313.

Scaltriti et al., Cyclin E amplification/overexpression is a mechanism of trastuzumab resistance in HER2+ breast cancer patients, Proc Natl Acad Sci.(2011) 108:3761-6.

Chinese priority application No. 2020105588231.

Jul. 9, 2024 First Office Action issued in Japanese Patent Application No. 2022-523308.

Aug. 9, 2024 First Office Action issued in European Patent Application No. 20877068.5.

* cited by examiner

AMINOPYRIMIDINE COMPOUND AS CDK2/4/6 TRIPLE INHIBITOR

CROSS-REFERENCE TO RELATED APPLICATIONS

This application is a U.S. National Phase Application under 35 U.S.C. 371 of International Application No. PCT/CN2020/121390, filed on Oct. 16, 2020, which claims the benefit of Chinese Patent Application No. 201910988432.0, filed on Oct. 17, 2019, and Chinese Patent Application No. 202010558823.1, filed on Jun. 18, 2020. The entire disclosures of the above applications are incorporated herein by reference.

The present application claims the following priorities:

CN 201910988432.0, filed on Oct. 17, 2019;

CN 202010558823.1, filed on Jun. 18, 2020.

TECHNICAL FIELD

The present disclosure relates to a novel aminopyrimidine compound as CDK2/4/6 inhibitor, specifically to a compound represented by formula (I) and a pharmaceutically acceptable salt thereof, and a use of the compound represented by formula (I) and the pharmaceutically acceptable salt thereof in the preparation of a medicament for treating solid tumor.

BACKGROUND

Malignant tumors are one of the major diseases that endanger human life safety nowadays. Over the past hundred years, mankind has developed a variety of diagnosis and treatment methods to combat malignant tumors, including the most commonly used chemotherapy, surgery, radiotherapy and targeted therapy. These therapies delay the development of the tumors to a certain extent and prolong the lives of patients. However, due to the characteristics of unrestricted growth, invasion and metastasis of the malignant tumors, the above therapies still unable to achieve the desired inhibitory effect. Meanwhile, the toxic and side effects of the above therapies are also a key factor limiting their application.

The regulation of the cell cycle is mainly affected by a series of serine/threonine kinases, also known as cyclin-dependent kinases (CDK), which are expected to associate with the corresponding regulatory subunit cyclins to promote the progress of the cell cycle, the transcription of genetic information and the normal division and proliferation of cells. Abnormal activation of CDK is associated with the development of tumor, and CDK inhibitors have been shown to be useful in tumor therapy. The CDK4/6 inhibitors Palbociclib, Abemaciclib and Ribociclib are currently approved for the treatment of HR-positive/HER-2-negative breast cancer. Although CDK4/6 inhibitors demonstrate good clinical efficacy in HR-positive metastatic breast cancer, their inhibitory activity against other CDK subtypes is weak and prone to primary and acquired drug resistance.

CDK2 overexpression is associated with the abnormal regulation of the cell cycle, and CDK2/Cyclin E is involved in the regulation of the cell cycle from G1 phase to S phase. At the end of G1 phase, the complex of CDK2/Cyclin E can also catalyze the phosphorylation of Rb, thereby promoting the progression of the cell cycle from G1 phase to S phase; in S phase, the complex of CDK2/cyclin A can promote the process of DNA replication. (Asghar et al. *The history and future of targeting cyclin-dependent kinases in cancer therapy*, Nat. Rev. Drug. Discov. 2015; 14(2):130-146) Cyclin E, the corresponding cyclin of CDK2, is commonly overexpressed in tumors. Amplification and overexpression of Cyclin E1 are associated with poor prognosis in tumors such as ovarian, gastric and breast cancers. (Nakayama et al., *Gene amplification CCNE1 is related to poor survival and potential therapeutic target in ovarian cancer*, cancer (2010) 116:2621-34; Etemadmoghadam et al., *Resistance to CDK2 inhibitors is associated with selection of polyploidy cells in CCNE1-Amplified Ovarian cancer*, clin cancer res (2013)19:5960-71; Au-Yeung et al., *selective targeting of cyclin E1-Amplified high-grade serous ovarian cancer by cyclin-dependent kinase 2 and AKT inhibition*, Clin. Cancer res. (2017) 30:297-303; Ooi et al., *Gene amplification of CCNE1, CCND1, and CDK6 in gastric cancers detected by multiplex ligation-dependent probe amplification and fluorescence in situ hybridization*, Hum Pathol. (2017) 61: 58-67; Noske et al., *detection of CCNE1/UR/(19q12) amplification by in situ hybridization is common in high grade and type 2 endometrial cancer*, oncotarget (2017) 8:14794-14805). Overexpression of Cyclin E2 is associated with resistance to endocrine therapy in breast cancer, and inhibition of CDK2 can resensitize tamoxifen-resistant and CCNE2-overexpressing cells to tamoxifen and CDK4/6 inhibitors. (caldon et al., *Cyclin E2 overexpression is associated with endocrine resistance but not insensitivity to CDK2 inhibition in human breast cancer cells.* Mol cancer Ther. (2012) 11:1488-99; Herrera-abreu et al., *Early adaption and acquired resistance to CDK4/6 inhibition in Estrogen Receptor-positive breast cancer*, cancer res. (2016) 76:2301-2313). Amplification of Cyclin E is also associated with trastuzumab resistance in HER2-positive breast cancer. (Scaltriti et al., *Cyclin E amplification/overexpression is a mechanism of trastuzumab resistance in HER2+ breast cancer patients*, Proc Natl Acad Sci. (2011) 108:3761-6).

The small-molecule CDK inhibitor dinaciclib simultaneously inhibits CDK1, CDK2, CDK5 and CDK9, and is currently undergoing clinical trials in breast cancer and hematological tumors. Seliciclib simultaneously inhibits CDK2, CDK7 and CDK9, and is currently undergoing clinical trials in combination with chemotherapy for the treatment of solid tumors. The CDK2/4/6 inhibitor PF-06873600 (WO2018033815A1) developed by Pfizer has been tested in clinical trials, and its CDK2 activity is high, but its selectivity to other CDK isoforms such as CDK9 is poor. So far, there are still no CDK2 inhibitors approved for marketing. Small-molecule drugs with CDK2 inhibitory activity and novel kinase inhibition profile remain an unmet clinical need.

PF-06873600

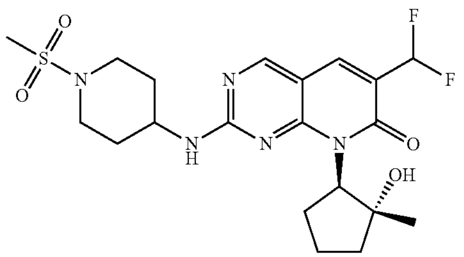

CONTENT OF THE PRESENT INVENTION

On the one hand, the present disclosure provides a compound represented by formula (I) or a pharmaceutically acceptable salt thereof,

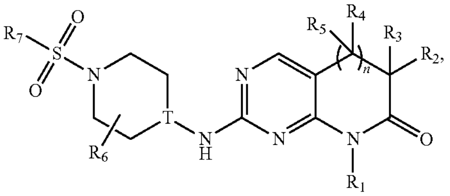

(I)

wherein,

T is N or CH;

$R_1$ is $C_{4-6}$ cycloalkyl, wherein the $C_{4-6}$ cycloalkyl is substituted with 1, 2 or 3 $R^a$;

each $R^a$ is independently F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

$R_2$ and $R_3$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_2$ and $R_3$ are joined together with the carbon atom to which they are attached form $C_{3-5}$ cycloalkyl, wherein the $C_{3-5}$ cycloalkyl is optionally substituted with 1, 2 or 3 $R^b$;

each $R^b$ is independently H, F, Cl, Br, I, —CN, —OH, $C_{1-3}$ alkoxy, $C_{1-3}$ alkyl or $C_{1-3}$ haloalkyl;

$R_4$ and $R_5$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_3$ and $R_4$ are joined together with the carbon atom to which they are attached form $C_{3-5}$ cycloalkyl, wherein the $C_{3-5}$ cycloalkyl is optionally substituted with 1, 2 or 3 $R^c$;

each $R^c$ is independently H, F, Cl, Br, I, —CN, —OH, $C_{1-3}$ alkoxy, $C_{1-3}$ alkyl or $C_{1-3}$ haloalkyl;

$R_6$ is H, F, Cl, Br, I, —CN, —OH, $C_{1-3}$ alkoxy, $C_{1-3}$ alkyl or $C_{1-3}$ haloalkyl;

$R_7$ is —$NH_2$, $C_{1-3}$ alkylamino, $C_{1-6}$ alkyl, $C_{3-5}$ cycloalkyl, 4- to 6-membered heterocycloalkyl, 5- to 6-membered heteroaryl or phenyl, wherein the $C_{1-6}$ alkyl, the $C_{3-5}$ cycloalkyl, the 4- to 6-membered heterocycloalkyl, the 5- to 6-membered heteroaryl and the phenyl are optionally substituted with 1, 2 or 3 $R^d$;

each $R^d$ is independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

n is 0, 1 or 2;

the 4- to 6-membered heterocycloalkyl and the 5- to 6-membered heteroaryl respectively comprise 1, 2, 3 or 4 heteroatoms independently selected from N, —O— and —S—.

The present disclosure also provides a compound represented by formula (I) or a pharmaceutically acceptable salt thereof,

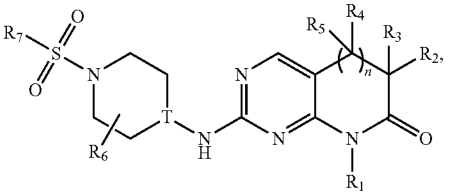

(I)

wherein,

T is N or CH;

$R_1$ is $C_{4-6}$ cycloalkyl, wherein the $C_{4-6}$ cycloalkyl is optionally substituted with 1, 2 or 3 $R^a$;

each $R^a$ is independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

$R_2$ and $R_3$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_2$ and $R_3$ are joined together with the carbon atom to which they are attached form $C_{3-5}$ cycloalkyl, wherein the $C_{3-5}$ cycloalkyl is optionally substituted with 1, 2 or 3 $R^b$;

each $R^b$ is independently H, F, Cl, Br, I, —CN, —OH, $C_{1-3}$ alkoxy, $C_{1-3}$ alkyl or $C_{1-3}$ haloalkyl;

$R_4$ and $R_5$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_3$ and $R_4$ are joined together with the carbon atom to which they are attached form $C_{3-5}$ cycloalkyl, wherein the $C_{3-5}$ cycloalkyl is optionally substituted with 1, 2 or 3 $R^c$;

each $R^c$ is independently H, F, Cl, Br, I, —CN, —OH, $C_{1-3}$ alkoxy, $C_{1-3}$ alkyl or $C_{1-3}$ haloalkyl;

$R_6$ is H, F, Cl, Br, I, —CN, —OH, $C_{1-3}$ alkoxy, $C_{1-3}$ alkyl or $C_{1-3}$ haloalkyl;

$R_7$ is —$NH_2$, $C_{1-3}$ alkylamino, $C_{1-6}$ alkyl, $C_{3-5}$ cycloalkyl, 4- to 6-membered heterocycloalkyl, 5- to 6-membered heteroaryl or phenyl, wherein the $C_{1-6}$ alkyl, the $C_{3-5}$ cycloalkyl, the 4- to 6-membered heterocycloalkyl, the 5- to 6-membered heteroaryl and the phenyl are optionally substituted with 1, 2 or 3 $R^d$;

each $R^d$ is independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

n is 0, 1 or 2;

the 4- to 6-membered heterocycloalkyl and the 5- to 6-membered heteroaryl respectively comprise 1, 2, 3 or 4 heteroatoms independently selected from N, —O— and —S—.

In some embodiments of the present disclosure, each of the above-mentioned $R^a$ is independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, each of the above-mentioned $R^a$ is independently F, Cl, Br, I, —CN, —OH, —$OCH_3$, —$CH_3$, —$CF_3$ or —$CH_2CH_3$, and other variables are as defined in the present disclosure.

In some embodiments of the present disclosure, the above-mentioned $R_1$ is

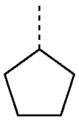
or
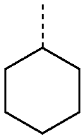
, wherein the

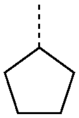
and
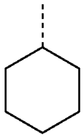

are optionally substituted with 1, 2 or 3 $R^a$, each $R^a$ and other variables are as defined in the present disclosure.

In some embodiments of the present disclosure, the above-mentioned $R_1$ is

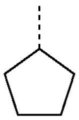
or
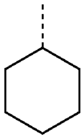
, wherein the

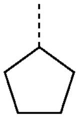
and
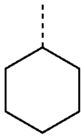

are substituted with 1, 2 or 3 $R^a$, each $R^a$ and other variables are as defined in the present disclosure.

In some embodiments of the present disclosure, the above-mentioned $R_1$ is

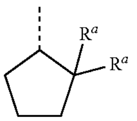
or
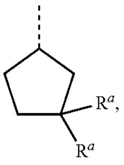

each $R^a$ and other variables are as defined in the present disclosure.

In some embodiments of the present disclosure, the above-mentioned $R_1$ is

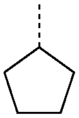
,
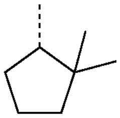
or
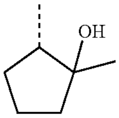
, and other variables are as defined in the present disclosure.

In some embodiments of the present disclosure, the above-mentioned $R_1$ is

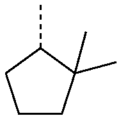
,
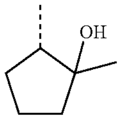
or
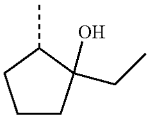
, and other variables are as defined in the present disclosure.

In some embodiments of the present disclosure, the above-mentioned compound has the structure represented by formula (I-1):

(I-1)

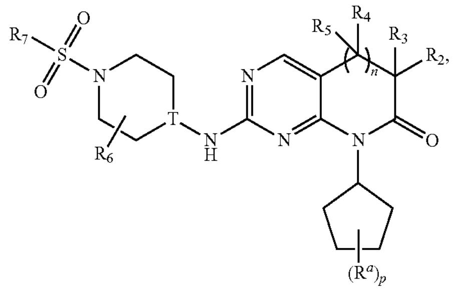

wherein, $R_2$, $R_3$, $R_4$, $R_5$, $R_6$, $R_7$, $R^a$ and n are as defined in the present disclosure, p is 0, 1, 2 or 3.

In some embodiments of the present disclosure, the above-mentioned compound has the structure represented by formula (I-1):

(I-1)

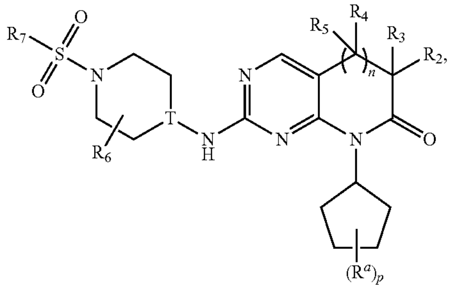

wherein, $R_2$, $R_3$, $R_4$, $R_5$, $R_6$, $R_7$, $R^a$ and n are as defined in the present disclosure, p is 1, 2 or 3.

In some embodiments of the present disclosure, the above-mentioned compound has the structure represented by formula (I-2):

(I-2)

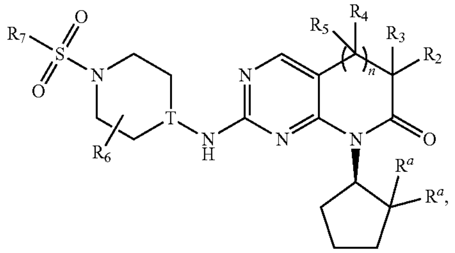

wherein, $R_2$, $R_3$, $R_4$, $R_5$, $R_6$, $R_7$, $R^a$ and n are as defined in the present disclosure.

In some embodiments of the present disclosure, each of the above-mentioned $R^b$ is independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, the above-mentioned $R_2$ and $R_3$ are joined together with the carbon atom to which they are attached form cyclopropyl, wherein the cyclopropyl is optionally substituted with 1, 2 or 3 $R^b$, each $R^b$ and other variables are as defined in the present disclosure.

In some embodiments of the present disclosure, the above-mentioned $R_4$ and $R_5$ are each independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, each of the above-mentioned $R^c$ is independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, the above-mentioned $R_3$ and $R_4$ are joined together with the carbon atom to which they are attached form cyclopropyl, wherein the cyclopropyl is optionally substituted with 1, 2 or 3 $R^c$, each $R^c$ and other variables are as defined in the present disclosure.

In some embodiments of the present disclosure, the above-mentioned compound has a structure represented by any structural formula of formula (I-3)-(I-7):

(I-3)

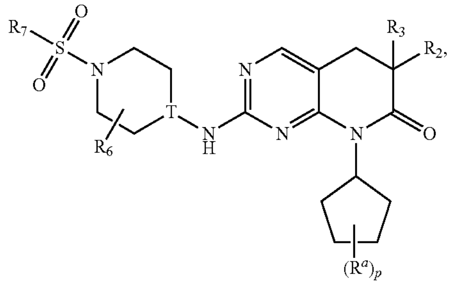

(I-4)

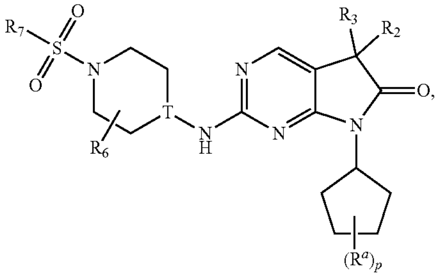

-continued (I-5)

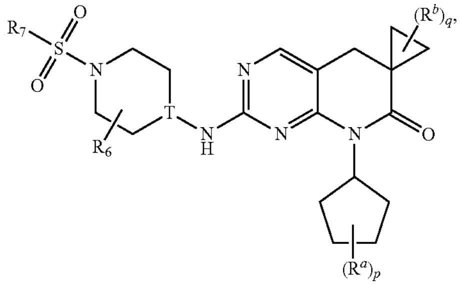

(I-6)

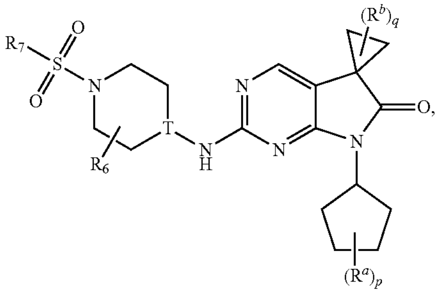

or (I-7)

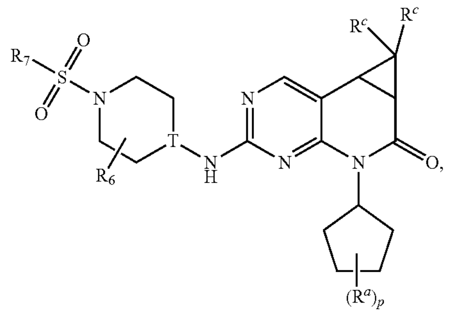

wherein, $R^a$, $R^b$, $R^c$, T, $R_6$, $R_7$ and p are as defined in the present disclosure, q is 0, 1, 2 or 3.

In some embodiments of the present disclosure, the above-mentioned compound has a structure represented by any structural formula of formula (I-8)-(I-12):

(I-8)

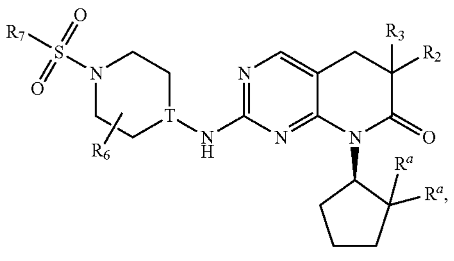

(I-9)

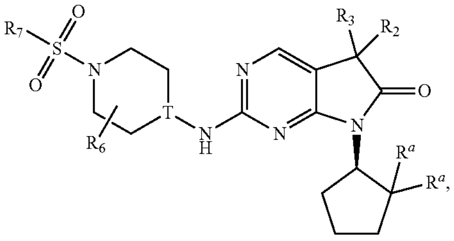

-continued (I-10)

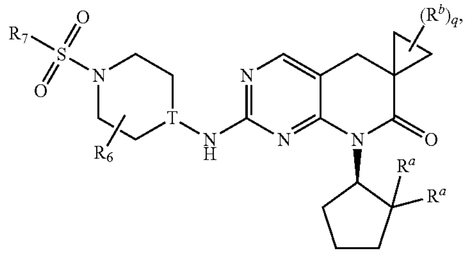

(I-11)

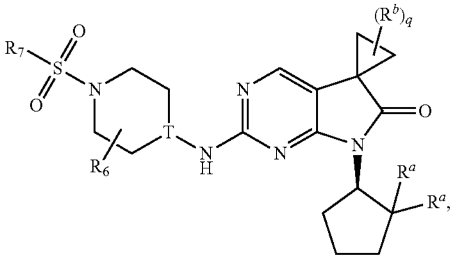

, or (I-12)

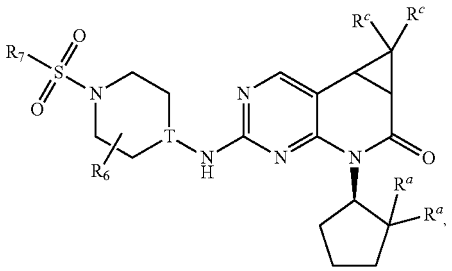

wherein, $R^a$, $R^b$, $R^c$, T, $R_6$, $R_7$, p and q are as defined in the present disclosure.

In some embodiments of the present disclosure, each of the above-mentioned $R_2$ and $R_3$ are each independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, $R_6$ is H, F, Cl, Br, I, —CN, —OH, —$OCH_3$, —$CH_3$, or —$CH_2CH_3$, and other variables are as defined in the present disclosure.

In some embodiments of the present disclosure, each of the above-mentioned $R_d$ is independently H, F, Cl, Br, I, —CN, —OH, —$OCH_3$, —$CH_3$, —$CF_3$ or —$CH_2CH_3$, and other variables are as defined in the present disclosure.

In some embodiments of the present disclosure, each of the above-mentioned $R^d$ is independently H, F, Cl, Br, I, —CN, —OH, —$OCH_3$, —$CH_3$, —$CF_3$, —$CH_2CH_3$ or —$CH(CH_3)_2$, and other variables are as defined in the present disclosure.

In some embodiments of the present disclosure, the above-mentioned $R_7$ is —$NH_2$, —$NH(CH_3)$, —NH($CH_2CH_3$), —$N(CH_3)_2$, —$CH_3$, —$CH_2CH_3$, —$CH_2CH_2CH_3$, —$CH(CH_3)_2$, cyclopropyl, cyclopentyl, pyrrolidinyl, tetrahydrofuranyl, piperidinyl, pyrazolyl, pyridyl or phenyl, wherein the —$CH_3$, the —$CH_2CH_3$, the —$CH_2CH_2CH_3$, the —$CH(CH_3)_2$, the cyclopropyl, the cyclopentyl, the pyrrolidinyl, the tetrahydrofuranyl, the piperidinyl, the pyrazolyl, the pyridyl and the phenyl are optionally substituted with 1, 2 or 3 $R^d$, each $R^d$ and other variables are as defined in the present disclosure.

In some embodiments of the present disclosure, the above-mentioned $R_7$ is —$NH_2$, —$NH(CH_3)$, —NH($CH_2CH_3$), —$N(CH_3)_2$, —$CH_3$, —$CH_2CH_3$, —$CH_2CH_2CH_3$, —$CH(CH_3)_2$, cyclopropyl, cyclopentyl, azacyclobutyl, pyrrolidinyl, tetrahydrofuranyl, piperidinyl, pyrazolyl, pyridyl or phenyl, wherein the —$CH_3$, the —$CH_2CH_3$, the —$CH_2CH_2CH_3$, the —$CH(CH_3)_2$, the cyclopropyl, the cyclopentyl, the azacyclobutyl, the pyrrolidinyl, the tetrahydrofuranyl, the piperidinyl, the pyrazolyl, the pyridyl or the phenyl are optionally substituted with 1, 2 or 3 $R^d$, each $R^d$ and other variables are as defined in the present disclosure.

In some embodiments of the present disclosure, the above-mentioned $R_7$ is —$NH_2$, —$NH(CH_3)$, —NH ($CH_2CH_3$), —$N(CH_3)_2$, —$C(R^d)_3$, —$CH_2CH_2R^d$,

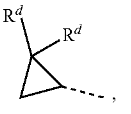
,
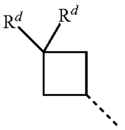
,
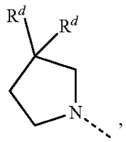
,
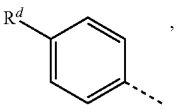
,
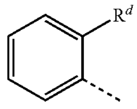
or
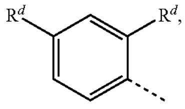

each $R^d$ and other variables are as defined in the present disclosure.

In some embodiments of the present disclosure, the above-mentioned $R_7$ is —$NH_2$, —$NH(CH_3)$, —NH ($CH_2CH_3$), —$N(CH_3)_2$, —$C(R^d)_3$, —$CH_2CH_2R^d$,

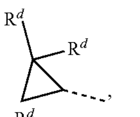
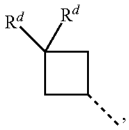
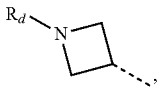
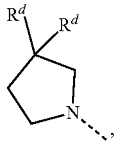
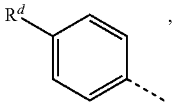
,
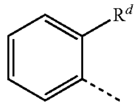
or
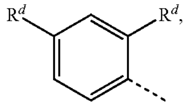

each $R^d$ and other variables are as defined in the present disclosure.

In some embodiments of the present disclosure, the above-mentioned $R_7$ is —$NH_2$, —$NH(CH_3)$, —NH ($CH_2CH_3$), —$N(CH_3)_2$, —$C(R^d)_3$, —$CH_2CH_2R^d$, —CH ($CH_3)_2$,

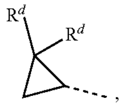
,
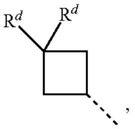
,
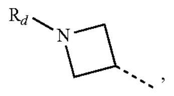
,
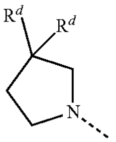
,
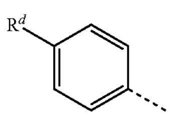
,
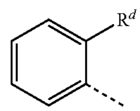
or
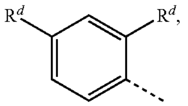

each $R^d$ and other variables are as defined in the present disclosure.

In some embodiments of the present disclosure, the above-mentioned $R_7$ is $-NH_2$, $-NH(CH_3)$, $-N(CH_3)_2$, $-CH_3$, $-CF_3$, $-CH_2CH_3$,

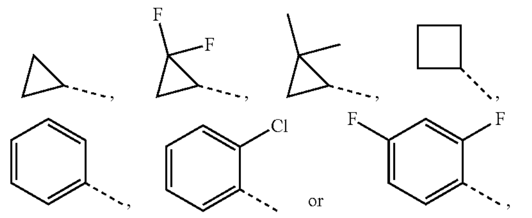

and other variables are as defined in the present disclosure.

In some embodiments of the present disclosure, the above-mentioned $R_7$ is $-NH_2$, $-NH(CH_3)$, $-N(CH_3)_2$, $-CH_3$, $-CF_3$, $-CH_2CH_3$,

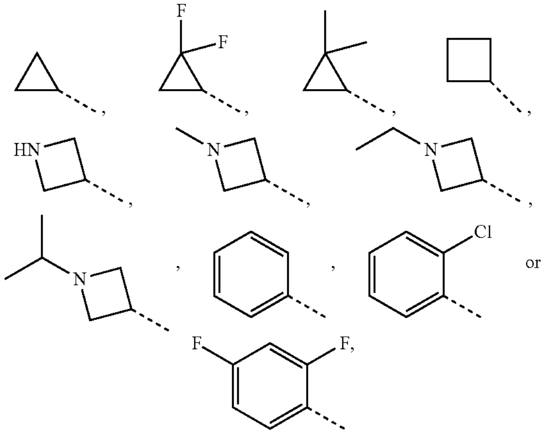

and other variables are as defined in the present disclosure.

In some embodiments of the present disclosure, the above-mentioned $R_7$ is $-NH_2$, $-NH(CH_3)$, $-N(CH_3)_2$, $-CH_3$, $-CF_3$, $-CH_2CH_3$, $-CH(CH_3)_2$, $-CH_2CH_2OCH_3$,

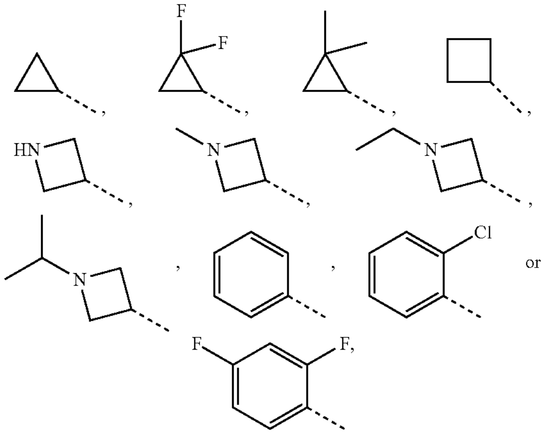

and other variables are as defined in the present disclosure.

Other embodiments of the present disclosure are generated by any combination of the above variables.

In some embodiments of the present disclosure, the above-mentioned compound is

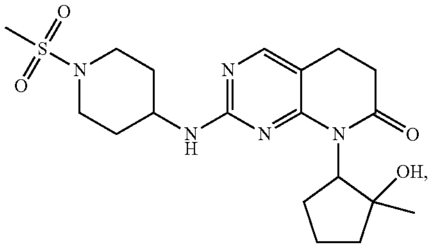

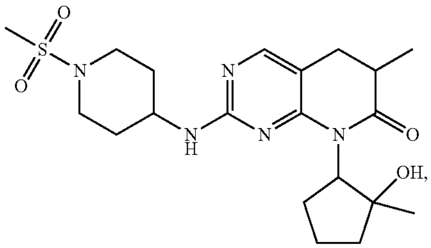

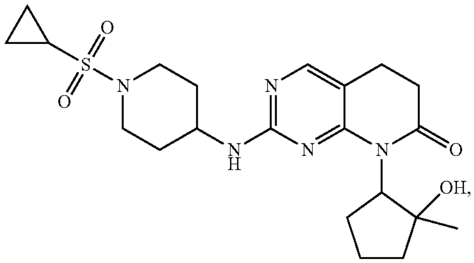

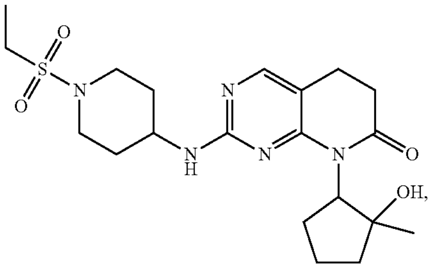

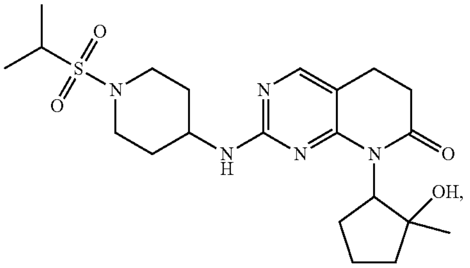

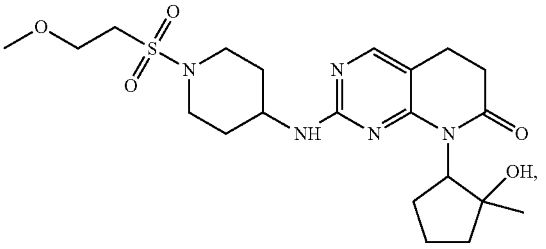

-continued
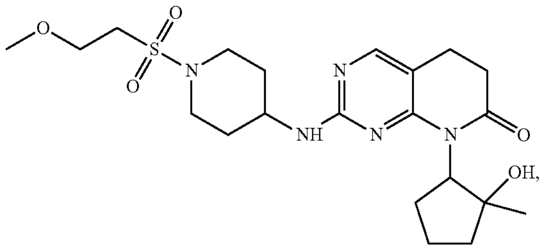
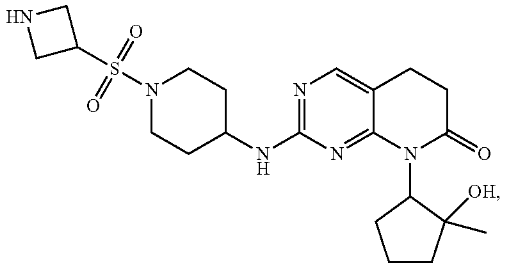
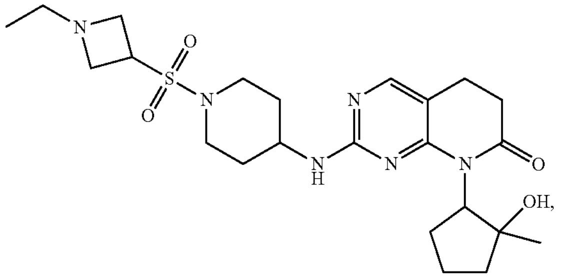
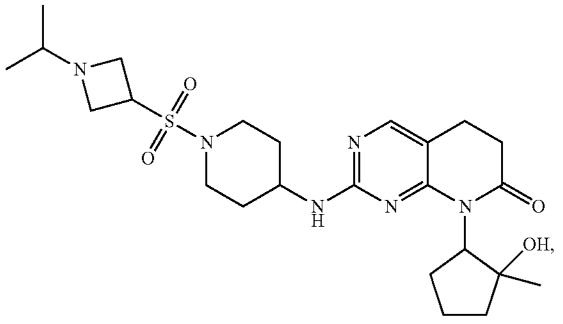
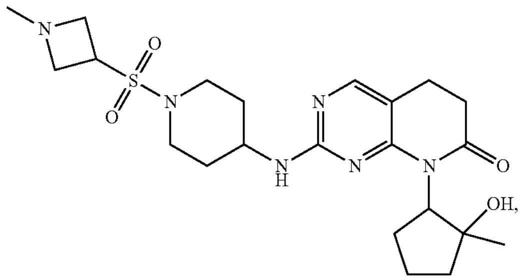
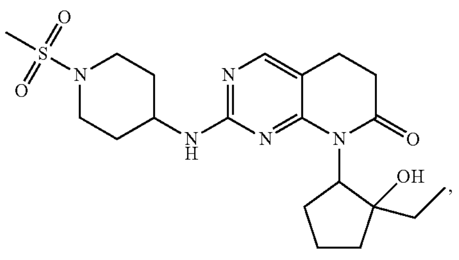
-continued
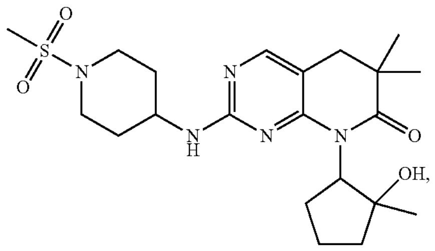
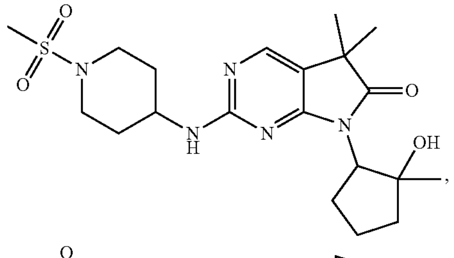
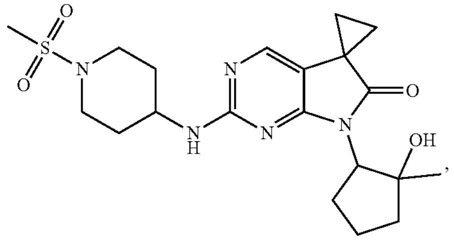
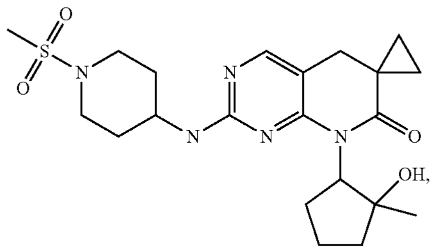
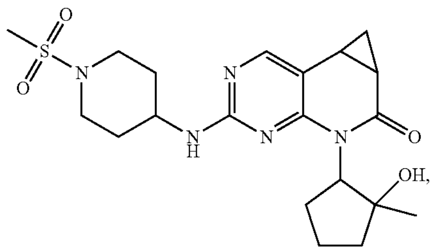
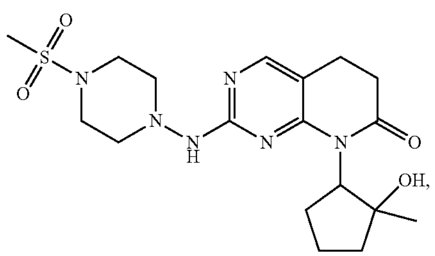
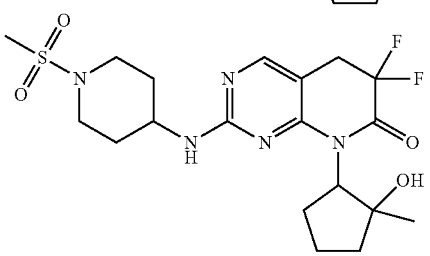
or -continued
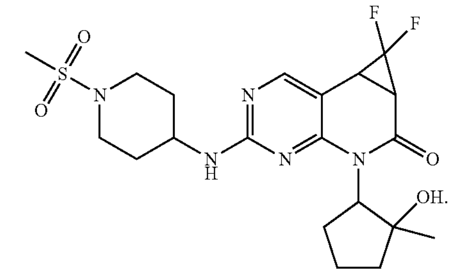
In some embodiments of the present disclosure, the above-mentioned compound is
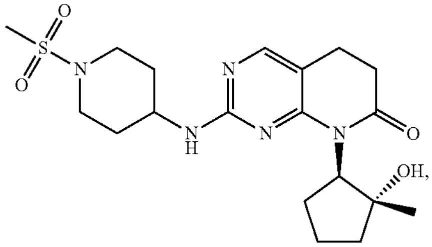
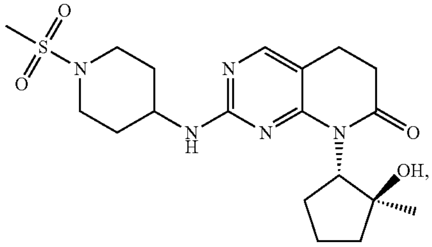
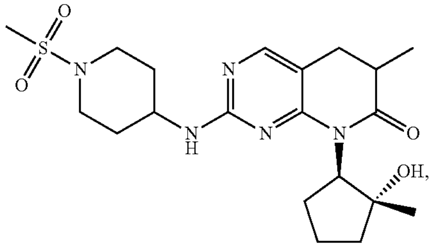
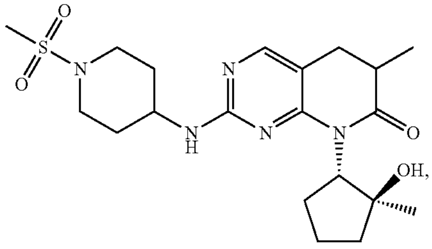
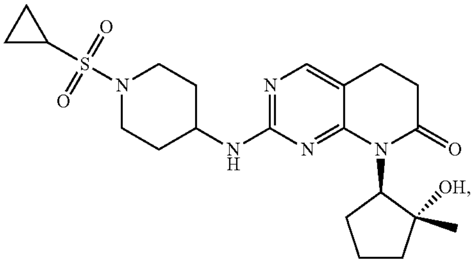
-continued
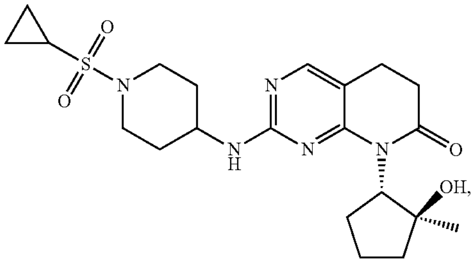
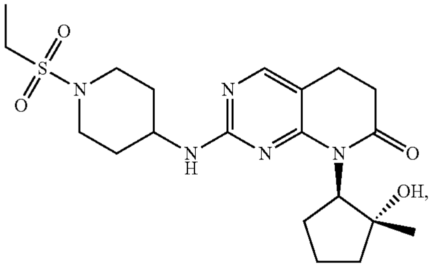
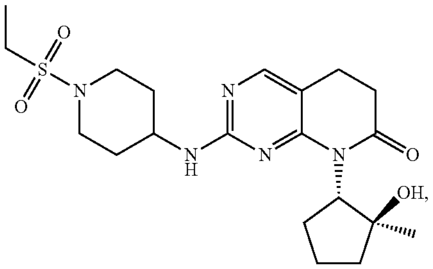
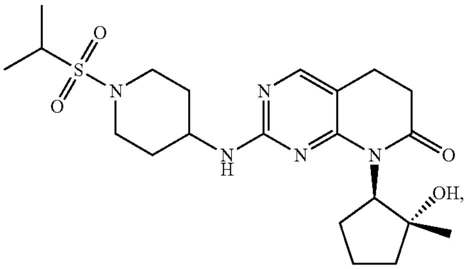
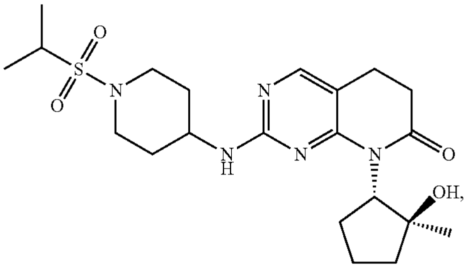
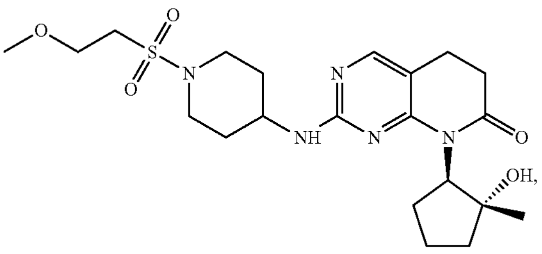

-continued
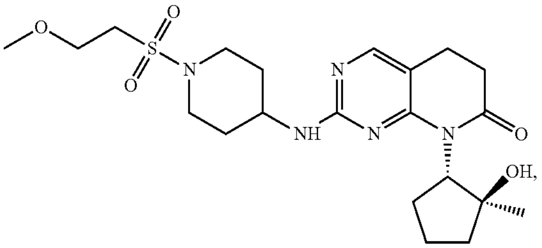
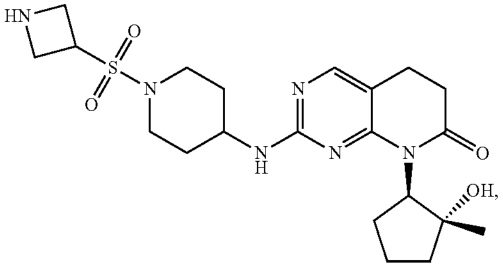
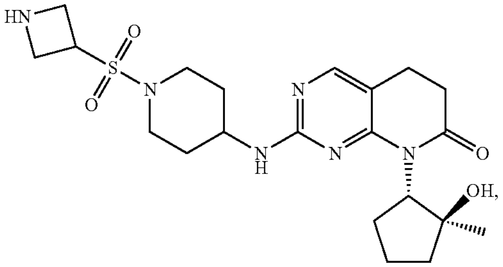
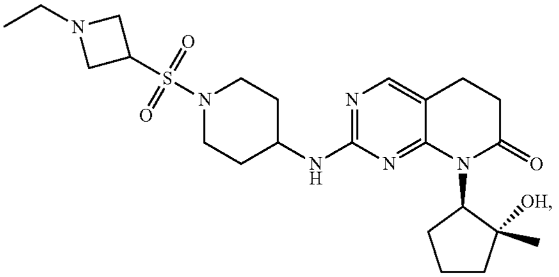
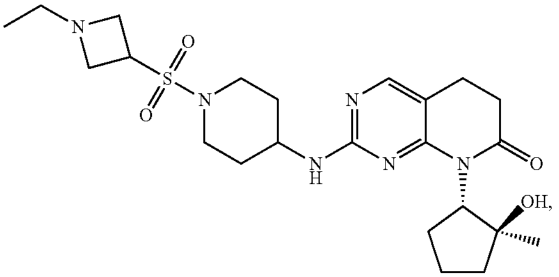
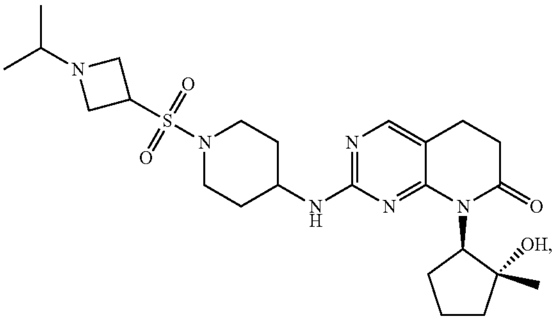
-continued
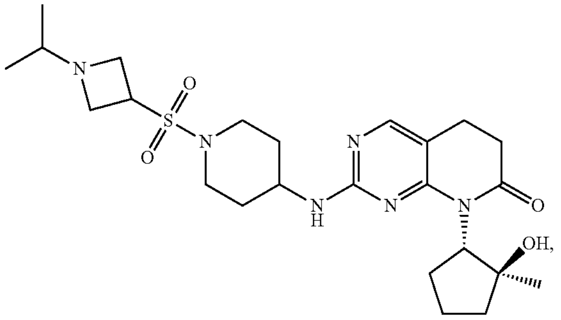
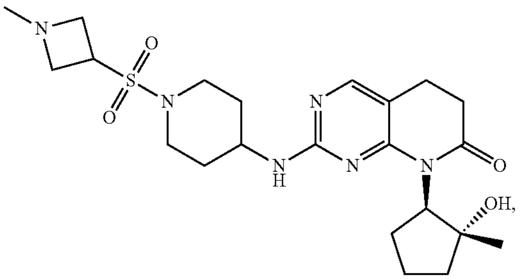
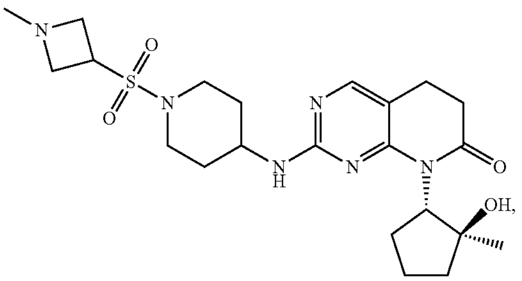
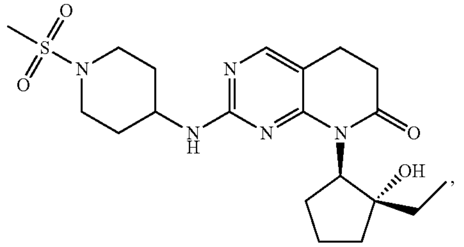
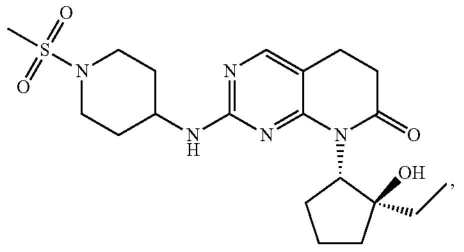
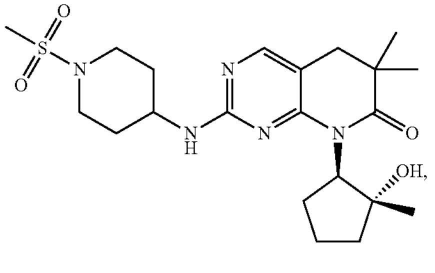

-continued

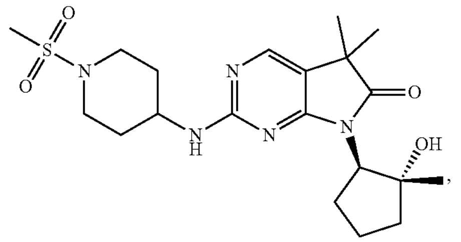

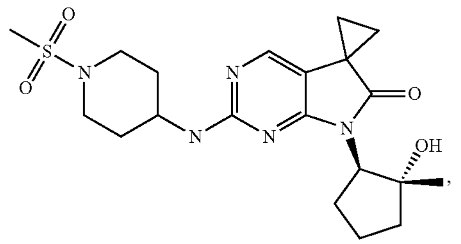

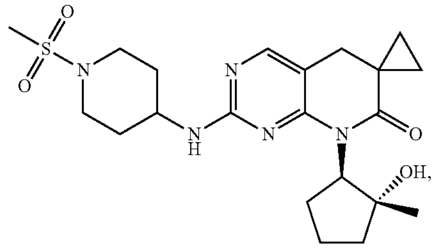

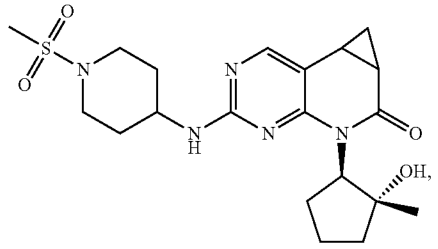

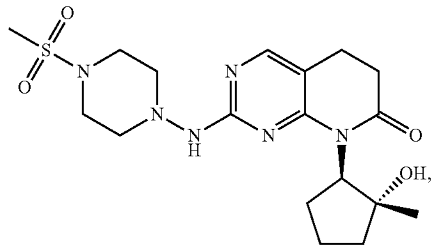

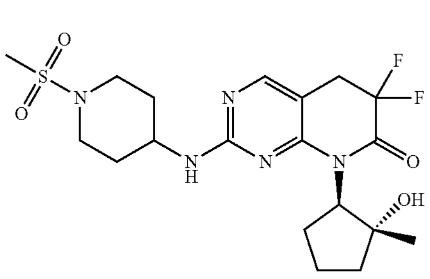

or

-continued

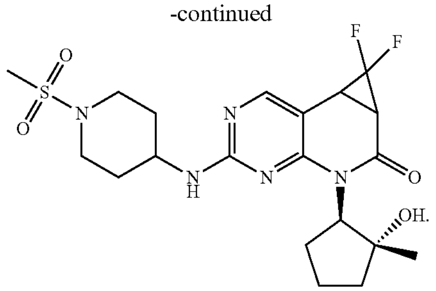

In some embodiments of the present disclosure, the above-mentioned pharmaceutically acceptable salt is hydrochloride salt.

The present disclosure also provides a pharmaceutical composition comprising a therapeutically effective amount of the above-mentioned compound or the pharmaceutically acceptable salt thereof and a pharmaceutically acceptable carrier.

On the other hand, the present disclosure also provides a use of the above-mentioned compound or the pharmaceutically acceptable salt thereof and the above-mentioned pharmaceutical composition in the preparation of a medicament of CDK2/4/6 inhibitor.

The present disclosure also provides a use of the above-mentioned compound or the pharmaceutically acceptable salt thereof and the above-mentioned pharmaceutical composition in the preparation of a medicament for treating solid tumor.

In some embodiments of the present disclosure, the above-mentioned solid tumor is colorectal cancer or breast cancer.

TECHNICAL EFFECT

The present disclosure provides a novel structure of CDK2/4/6 triple inhibitor. The compound of this series has excellent inhibitory activity on the enzyme level of CDK2/4/6, and the selectivity of CDK9 is significantly better than that of PF-06873600, the safety risk caused by off-target is low. It has significant inhibitory activity on the proliferation of colorectal cancer cells HCT116 and triple-negative breast cancer cells HCC1806 with high Cyclin E expression levels, and the selectivity of Rb-negative triple-negative breast cancer cells MDA-MB-468 is significantly better than that of PF-06873600. The compound of the present disclosure also has lower clearance rate, higher AUC, higher oral bioavailability and better comprehensive pharmacokinetic properties.

Definition and Description

Unless otherwise specified, the following terms and phrases used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereocenter is represented by a wedged solid bond ( ) and a wedged dashed bond ( ) and the relative configuration of stereocenter is represented by a straight solid bond ( ) and a straight dashed bond ( ), a wave line ( ) is used to represent a wedged solid bond ( ) or a wedged dashed bond ( ), or the wave line ( ) is used to represent a straight solid bond ( ) and a straight dashed bond ( ).

The compound of the present invention may exist in particular. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure. "optional" or "optionally" means that the subsequent event or condition may occur but not requisite, that the term includes the instance in which the event or condition occurs and the instance in which the event or condition does not occur.

For a drug or pharmacologically active agent, the term "effective amount" or "therapeutically effective amount" refers to an amount of the drug or agent that is nontoxic but sufficient to achieve the desired effect. For oral dosage forms of the present disclosure, an "effective amount" of one active substance in a composition refers to the amount required to achieve the desired effect when combined with another active substance in the composition. Determination of the effective amount will vary from person to person, depending on the age and general condition of the recipient, and also on the particular active substance, and suitable effective amounts in each case may be determined by one skilled in the art according to routine experimentation.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as is chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

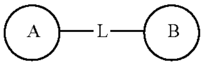

is -M-W—, then -M-W— can link ring A and ring B to form

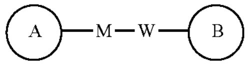

in the direction same as left-to-right reading order, and form

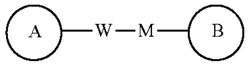

in the direction contrary to left-to-right reading order. A combination of the linking groups, substituents and/or variables thereof is allowed only when such combination can result in a stable compound.

Unless otherwise specified, when a group has one or more linkable sites, any one or more of the sites of that group may be linked to other groups by chemical bonding. The chemical bond between the site and other groups can be represented by a straight solid bond (  ), a straight dashed bond (  ) or a wavy line

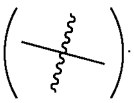

For example, the straight solid bond in $-OCH_3$ means that it is linked to other groups through the oxygen atom in the group; the straight dashed bonds in

means that it is linked to other groups through the two ends of nitrogen atom in the group; the wave lines in

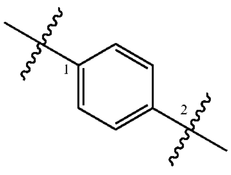 [SMILES: *c1ccc(*)cc1]

means that the phenyl group is linked to other groups through carbon atoms at position 1 and position 2.

Unless otherwise specified, the number of atoms in a ring is generally defined as the number of ring members, e.g., "5- to 7-membered ring" refers to a "ring" of 5-7 atoms arranged around it.

Unless otherwise specified, the term "$C_{1-6}$ alkyl" refers to a linear or branched saturated hydrocarbon group having 1 to 6 carbon atoms. The $C_{1-6}$ alkyl group includes $C_{1-5}$, $C_{1-4}$, $C_{1-3}$, $C_{1-2}$, $C_{2-6}$, $C_{2-4}$, $C_6$ and $C_5$ alkyl groups and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl and the like.

Unless otherwise specified, the term "$C_{1-4}$ alkyl" refers to a linear or branched saturated hydrocarbon group having 1 to 4 carbon atoms. The $C_{1-4}$ alkyl group includes $C_{1-2}$, $C_{1-3}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), butyl (including n-butyl, isobutyl, s-butyl and t-butyl) and the like.

Unless otherwise specified, the term "$C_{1-3}$ alkyl" refers to a linear or branched saturated hydrocarbon group having 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, the term "$C_{1-3}$ alkylamino" refers to an alkyl containing 1 to 3 carbon atoms connected to the rest of the molecule through an amino. The $C_{1-3}$ alkylamino includes $C_{1-2}$, $C_3$ and $C_2$ alkylamino and the like. Examples of $C_{1-3}$ alkylamino include, but are not limited to, $—NHCH_3$, $—N(CH_3)_2$, $—NHCH_2CH_3$, $—N(CH_3)CH_2CH_3$, $—NHCH_2CH_2CH_3$, $—NHCH_2(CH_3)_2$, and the like.

Unless otherwise specified, the term "halo" or "halogen" refers to a fluorine, chlorine, bromine or iodine atom by itself or as part of another substituent.

Unless otherwise specified, the term "$C_{1-3}$ haloalkyl" represents monohaloalkyl and polyhaloalkyl containing 1 to 3 carbon atoms. The $C_{1-3}$ haloalkyl group includes $C_{1-2}$, $C_{2-3}$, $C_3$, $C_2$, and $C_1$ haloalkyl, etc. Examples of $C_{1-3}$ haloalkyl include, but are not limited to, trifluoromethyl, trichloromethyl, 2,2,2-trifluoroethyl, pentafluoroethyl, pentachloroethyl, 3-bromopropyl, etc.

Unless otherwise specified, "$C_{4-6}$ cycloalkyl" refers to a saturated cyclic hydrocarbon group consisting of 4 to 6 carbon atoms, including monocyclic and bicyclic ring systems. The $C_{4-6}$ cycloalkyl includes $C_{4-5}$ and $C_{5-6}$ cycloalkyl and the like; it may be monovalent, divalent or polyvalent. Examples of $C_{4-6}$ cycloalkyl include, but are not limited to, cyclobutyl, cyclopentyl, cyclohexyl, and the like.

Unless otherwise specified, "$C_{3-5}$ cycloalkyl" refers to a saturated cyclic hydrocarbon group consisting of 3 to 5 carbon atoms, including monocyclic and bicyclic ring systems. The $C_{3-5}$ cycloalkyl includes $C_{3-4}$ and $C_{4-5}$ cycloalkyl and the like; it may be monovalent, divalent or polyvalent. Examples of $C_{3-5}$ cycloalkyl include, but are not limited to, cyclopropyl, cyclobutyl, cyclopentyl, and the like.

Unless otherwise specified, the term "4- to 6-membered heterocycloalkyl" by itself or in combination with other terms refers to a saturated cyclic group consisting of 4 to 6 ring atoms; 1, 2, 3, or 4 ring atoms of which are heteroatoms independently selected from O, S and N, and the remaining ring atoms are carbon atoms; wherein the nitrogen atom is optionally quaternized, and the nitrogen and sulfur heteroatoms may optionally be oxidized (i.e., NO and $S(O)_p$, p is 1 or 2). It includes monocyclic and bicyclic ring systems, wherein bicyclic ring system includes spiro ring, fused ring, and bridged ring. In addition, in terms of the "4- to 6-membered heterocycloalkyl", the heteroatom can occupy the position of attachment of the heterocycloalkyl to the rest of the molecule. The 4- to 6-membered heterocycloalkyl includes 5- to 6-membered, 4-membered, 5-membered, and 6-membered heterocycloalkyl and the like. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl, etc.), tetrahydrofuranyl (including tetrahydrofuran-2-yl, etc.), tetrahydropyranyl, piperidinyl (including 1-piperidinyl, 2-piperidinyl, and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, or homopiperidinyl, and the like.

Unless otherwise specified, the terms "5- to 6-membered heteroaromatic ring" and "5- to 6-membered heteroaryl" are used interchangeably herein, and the term "5- to 6-membered heteroaryl" refers to a monocyclic group consisting of 5 to 6 ring atoms having a conjugated π-electron system; 1, 2, 3 or 4 ring atoms of which are heteroatoms independently selected from O, S and N, and the remaining ring atoms are carbon atoms. Wherein the nitrogen atoms are optionally quaternized, and the nitrogen and sulfur heteroatoms may optionally be oxidized (i.e., NO and $S(O)_p$, p is 1 or 2). The 5- to 6-membered heteroaryl may be attached to the rest of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl, and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl, and 5-isoxazolyl, etc.), thiazolyl (including 2-thiazolyl, 4-thiazolyl, and 5-thiazolyl, etc.), furanyl (including 2-furanyl and 3-furanyl, etc.), thienyl (including 2-thienyl and 3-thienyl, etc.), pyridinyl (including 2-pyridinyl, 3-pyridinyl, and 4-pyridinyl, etc.), pyrazinyl, or pyrimidinyl (including 2-pyrimidinyl and 4-pyrimidinyl, etc.).

Unless otherwise specified, the terms "$C_{6-10}$ aromatic ring" and "$C_{6-10}$ aryl" are used interchangeably herein, and the terms "$C_{6-10}$ aromatic ring" or "$C_{6-10}$ aryl" refers to a cyclic hydrocarbon group consisting of 6 to 10 carbon atoms having a conjugated π-electron system. It may be a monocyclic, fused bicyclic, or fused tricyclic ring system, wherein each ring is aromatic. It can be monovalent, divalent, or polyvalent, and $C_{6-10}$ aryl includes $C_{6-9}$, $C_9$, $C_{10}$, and $C_6$ aryl, and the like. Examples of $C_{6-10}$ alkyl include, but are not limited to, phenyl, naphthyl (including 1-naphthyl and 2-naphthyl, etc).

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

The term “leaving group” refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term “protecting group” includes, but is not limited to “amino protecting group”, “hydroxy protecting group” or “thio protecting group”. The term “amino protecting group” refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term “hydroxy protecting group” refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available.

The following abbreviations are used in the present disclosure: DIBAL-H refers to diisobutylaluminum hydride; DMSO refers to dimethyl sulfoxide; DBU refers to 1,8-diazabicycloundec-7-ene; EDTA refers to ethylenediaminetetraacetic acid; HPMC refers to hydroxypropyl methylcellulose; LCMS refers to liquid chromatography mass spectrometry; $Rh(PPh_3)_3Cl$ refers to tris(triphenylphosphine) rhodium chloride; SFC refers to supercritical fluid chromatography; TLC refers to thin layer chromatography; $Pd(dppf)Cl_2 \cdot CH_2Cl_2$ refers to [1,1'-bis(diphenylphosphino) ferrocene]palladium dichloride dichloromethane; Psi refers to pounds/inch; DMSO refers to dimethyl sulfoxide; ATP refers to adenosine triphosphate; ADP-Glo refers to a kit.

DETAILED DESCRIPTION OF THE PREFERRED EMBODIMENT

The following embodiments describe the present disclosure in detail, but they are not meant to impose any unfavorable limitation on the present disclosure. The present disclosure has been described in detail herein, and its specific embodiments are also disclosed. It will be apparent to those skilled in the art that various changes and modifications can be made to the specific embodiments without departing from the spirit and scope of the present disclosure.

Example 1: Compound 1, Compound 1A and Compound 1B

1

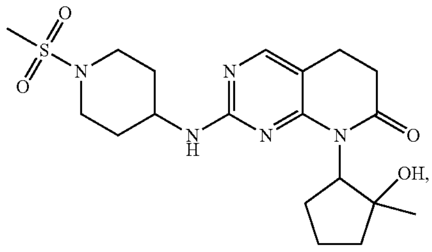

1A

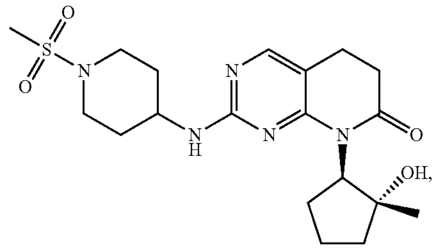

1B

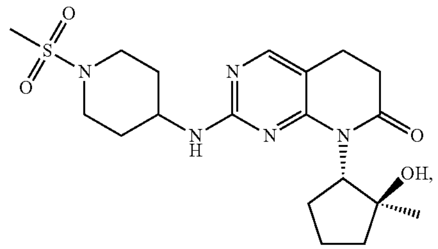

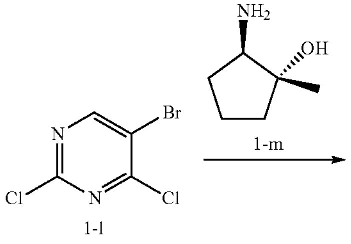

1-1

-continued

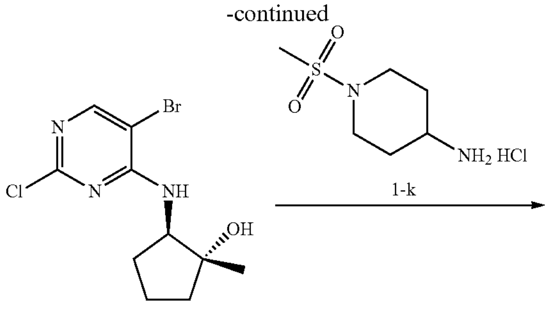

1-n

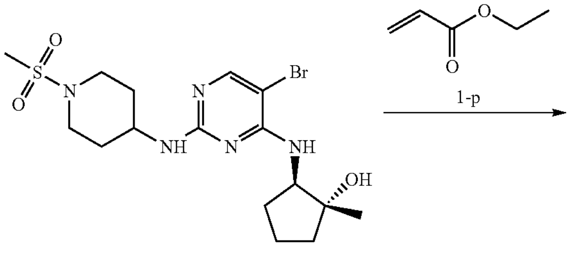

1-o

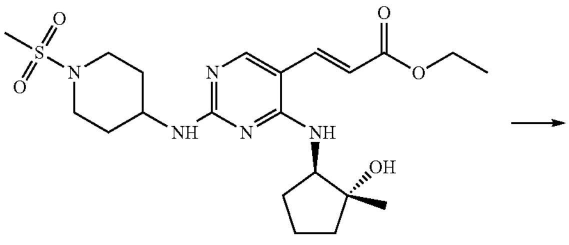

1-q

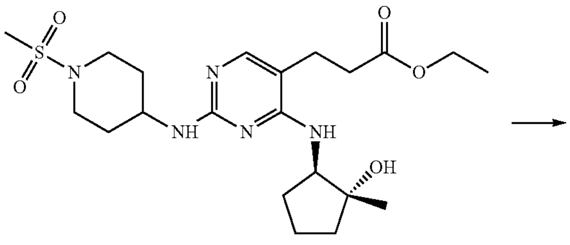

1-r

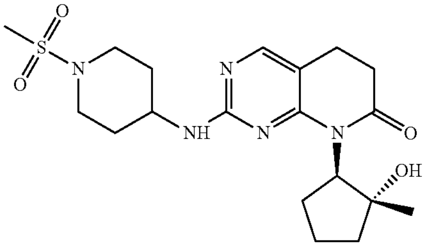

1A

Synthesis of Compound 1-n

Compound 1-1 (100 g, 438.84 mmol, 56.18 mL) was added to acetonitrile (1 L), then triethylamine (66.61 g, 658.26 mmol, 91.62 mL) was added, the mixture was cooled to 0° C., and compound 1-m (60.65 g, 526.61 mmol) was slowly added dropwise, keeping the temperature of the reaction system at 0-5° C., the reaction solution was stirred at 0-5° C. for 3 hours. The reaction system was added with water (500 mL) and extracted with ethyl acetate (500 mL×3), the organic phases were combined, washed with saturated brine (600 mL×3), dried over anhydrous sodium sulfate, and filtered, the filtrate was evaporated to dryness. The crude product was suspended and stirred with petroleum ether:ethyl acetate=10:1 (500 mL) at 20° C. for 2 hours, and filtered to obtain compound 1-n. $^1$H NMR (400 MHz, $CDCl_3$): δ 8.19 (s, 1H), 5.50 (br d, J=2.6 Hz, 1H), 4.36 (br s, 1H), 4.23 (ddd, J=5.7, 8.1, 10.2 Hz, 1H), 2.36-2.28 (m, 1H), 2.08-1.99 (m, 1H), 1.91-1.75 (m, 3H), 1.62-1.55 (m, 1H), 1.17 (s, 3H); LCMS (ESI): m/z: 308.0 (M+1).

Synthesis of Compound 1-0

Compound 1-n (110 g, 358.79 mmol) and compound 1-k (115.56 g, 538.19 mmol, HCl) were added to dimethyl sulfoxide (1100 mL), followed by potassium carbonate (148.76 g, 1.08 mol), the mixture was stirred at 120° C. for 16 hours. The mixture was cooled to 20° C., added with water (1 L), and extracted with ethyl acetate (500 mL×3), the organic phases were combined, washed with saturated brine (800 mL×3), dried over anhydrous sodium sulfate, and filtered, the filtrate was evaporated to dryness. The obtained crude product was stirred with ethyl acetate:petroleum ether=2:3 (500 mL) at 70° C. for 30 minutes, then cooled to 20° C. and stirred for 3 hours, and filtered to obtain compound 1-o. LCMS (ESI): m/z: 450.0 (M+1).

Synthesis of Compound 1-q

Compound 1-o (100 g, 218.77 mmol, 98.09% purity) was added to N,N-dimethylformamide (1000 mL), ethyl acrylate (219.02 g, 2.19 mol, 237.81 mL) was added, followed by triethylamine (88.55 g, 875.07 mmol, 121.80 mL) and Pd(dppf)$Cl_2CH_2Cl_2$ (17.87 g, 21.88 mmol), the mixture was purged with nitrogen several times, heated to 100° C. and stirred for 16 hours under nitrogen protection. The reaction solution was cooled to 20° C., added with water (1000 mL), and extracted with ethyl acetate (800 mL×3), the organic phases were combined, washed with saturated brine (500 mL×4), dried over anhydrous sodium sulfate, and filtered, the filtrate was evaporated to dryness. The crude product was stirred with methyl tert-butyl ether (500 mL) at 20° C. for 16 hours, added with petroleum ether (200 mL) to continue stirring for 3 hours, and filtered to obtain compound 1-q. $^1$H NMR (400 MHz, $CD_3OD$): δ 7.98 (s, 1H), 5.28 (br t, J=8.5 Hz, 1H), 4.15 (quin, J=7.6 Hz, 1H), 3.95-3.88 (m, 1H), 3.74 (br dd, J=3.7, 12.4 Hz, 2H), 3.68 (t, J=8.5 Hz, 2H), 3.46 (t, J=8.1 Hz, 2H), 3.02 (br t, J=11.7 Hz, 2H), 2.77-2.71 (m, 2H), 2.65-2.56 (m, 4H), 2.53-2.43 (m, 1H), 2.24-2.04 (m, 4H), 1.95-1.86 (m, 2H), 1.79-1.72 (m, 1H), 1.62-1.49 (m, 2H), 1.18 (s, 3H), 1.00 (t, J=7.2 Hz, 3H); LCMS (ESI): m/z: 468.1 (M+1).

Synthesis of Compound 1-r

Compound 1-q (101 g, 210.30 mmol, 97.36% purity) was added to ethanol (1000 mL), wet Pd/C (10%, 10 g) was added under nitrogen protection, and the reaction system was purged with hydrogen several times. The reaction solution was stirred at 80° C. for 32 hours under hydrogen (15 psi). The mixture was cooled to 20° C., filtered, and the filtrate was evaporated to dryness to obtain the crude product. The crude product was stirred with methyl tert-butyl ether (500 mL) at room temperature for 3 hours, and filtered to obtain compound 1-r. $^1$H NMR (400 MHz, $CD_3OD$): δ 7.56 (s, 1H), 4.36 (t, J=8.3 Hz, 1H), 4.13 (q, J=7.2 Hz, 2H), 3.79 (tt, J=4.0, 10.6 Hz, 1H), 3.74-3.67 (m, 2H), 2.95 (dt, J=2.6, 11.9 Hz, 2H), 2.87 (s, 3H), 2.73-2.67 (m, 2H), 2.58-2.52 (m, 2H), 2.23-2.04 (m, 3H), 1.90-1.72 (m, 5H), 1.64-1.53 (m, 2H), 1.24 (t, J=7.2 Hz, 3H), 1.16 (s, 3H); LCMS (ESI): m/z: 470.3 (M+1).

Synthesis of Compound 1A

Compound 1-r (7.8 g, 16.61 mmol) was added to dimethyl sulfoxide (80 mL), followed by DBU (5.06 g, 33.22 mmol, 5.01 mL). The mixture was heated to 120° C. and stirred for 10 hours. The reaction was cooled to 20° C., added with water (100 mL), and extracted with ethyl acetate (100 mL×2), the organic phases were combined, washed with saturated brine (100 mL×2), dried over anhydrous sodium sulfate, and filtered, the filtrate was concentrated under reduced pressure. The crude product was purified by preparative chromatography (Column: Waters Xbridge BEH C18 50×50 mm×10 μm; mobile phase: 0.05% aqueous ammonia solution as mobile phase A, acetonitrile as mobile phase B, B %: 20%-42%, gradient time: 15 min) to obtain compound 1A. $^1$H NMR (400 MHz, DMSO-$d_6$): δ 8.00 (s, 1H), 5.24-5.11 (m, 1H), 4.22 (s, 1H), 3.90-3.73 (m, 1H), 3.61-3.46 (m, 2H), 2.92-2.78 (m, 5H), 2.66-2.58 (m, 2H), 2.56-2.51 (m, 2H), 2.35-2.22 (m, 1H), 2.09-1.85 (m, 5H), 1.81-1.70 (m, 2H), 1.65-1.43 (m, 3H), 1.11-0.99 (m, 3H); LCMS (ESI): m/z: 424.2 (M+1).

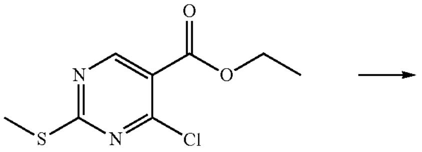

1-a

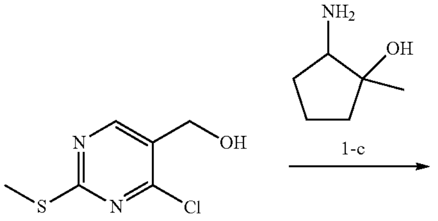

1-b

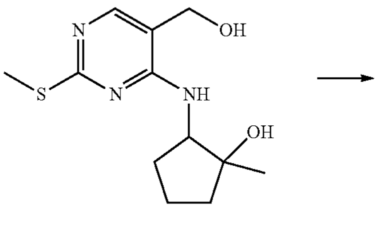

1-d

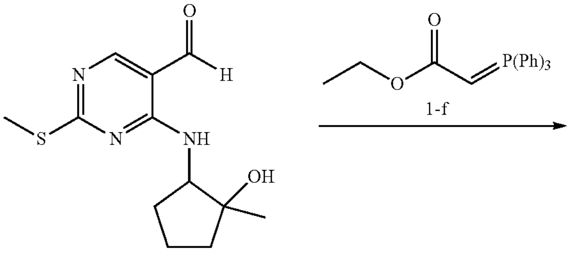

1-e

-continued

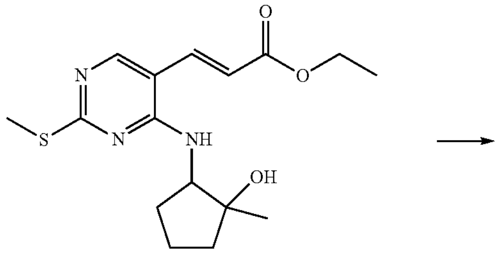

1-g

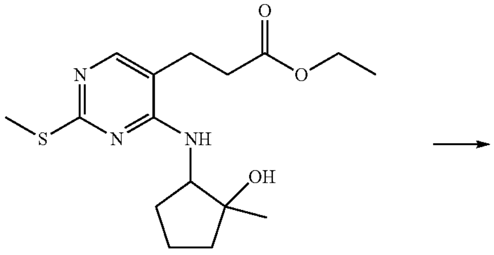

1-h

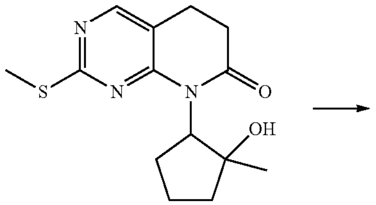

1-i

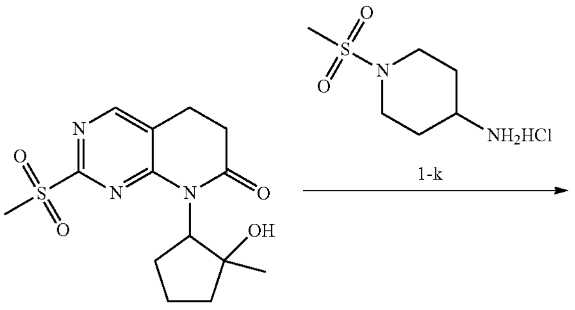

1-j

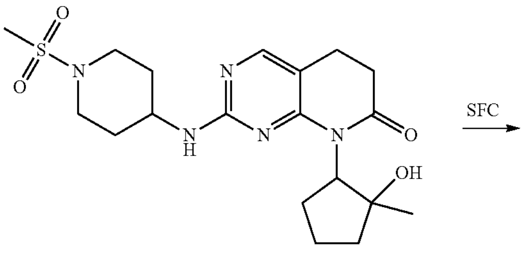

1

-continued

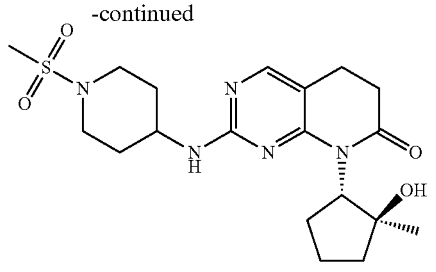

1B

Synthesis of Compound 1-B

Compound 1-a (100 g, 429.76 mmol) was added to tetrahydrofuran (1000 mL), cooled to −78° C., DIBAL-H (1 M, 859.52 mL) was slowly added dropwise under nitrogen protection, the reaction solution was warmed to 25° C. and stirred for 16 hours under nitrogen protection. TLC (petroleum ether:ethyl acetate=3:1) showed that a small amount of compound 1-a remained and a new product was formed. The reaction was stopped, quenched with saturated ammonium chloride (800 mL), extracted with ethyl acetate (500 mL×3), the organic phases were combined, washed with saturated brine (500 mL×2), dried over anhydrous sodium sulfate, and filtered, the filtrate was concentrated under reduced pressure, and the obtained crude product was stirred at 25° C. for 16 hours in petroleum ether:ethyl acetate=10:1 (200 mL) to obtain compound 1-b. $^1$H NMR (400 MHz, $CDCl_3$): 8.57 (s, 1H), 4.76 (s, 2H), 2.59 (s, 3H).

Synthesis of Compound 1-d

Compound 1-b (20 g, 104.90 mmol) and compound 1-c (12.69 g, 110.15 mmol) were added to acetonitrile (200 mL), and then triethylamine (15.92 g, 157.36 mmol, 21.90 mL) was added, the reaction solution was stirred at 80° C. for 12 hours. TLC (petroleum ether:ethyl acetate=3:1) showed that compound 1-b was reacted completely and a new product was formed. The reaction solution was cooled to 25° C. and concentrated under reduced pressure to remove excess acetonitrile. The obtained crude product was purified by silica gel column chromatography (petroleum ether/ethyl acetate=1/1) to obtain compound 1-d. $^1$H NMR (400 MHz, $CDCl_3$): 7.71 (s, 1H), 4.25 (m, 1H), 3.49 (s, 3H), 2.50 (s, 3H), 2.21 (dt, J=3.8, 8.1 Hz, 1H), 1.96 (dt, J=3.6, 7.7 Hz, 1H), 1.90-1.77 (m, 4H), 1.76-1.68 (m, 1H), 1.58-1.49 (m, 1H), 1.11 (s, 3H).

Synthesis of Compound 1-e

Compound 1-d (20 g, 74.25 mmol) was added to ethyl acetate (150 mL) and methanol (50 mL), then active manganese dioxide (64.55 g, 742.50 mmol) was added, and the reaction solution was stirred at 50° C. for 4 hours. TLC (petroleum ether:ethyl acetate=1:1) showed that compound 1-d was reacted completely and a new product was formed. The reaction solution was cooled to 25° C., and filtered, the filter cake was washed with methanol (50 mL×2), and the filtrate was concentrated under reduced pressure to obtain compound 1-e. $^1$H NMR (400 MHz, $CDCl_3$): 9.65 (s, 1H), 8.27 (s, 1H), 4.31 (ddd, J=6.5, 8.2, 9.5 Hz, 1H), 2.49 (s, 3H), 2.26-2.15 (m, 1H), 1.92-1.85 (m, 1H), 1.81-1.73 (m, 2H), 1.67-1.50 (m, 2H), 1.09 (s, 3H).

Synthesis of Compound 1-g

Compound 1-e (5 g, 18.70 mmol) was added to dichloromethane (100 mL), then compound 1-f (6.84 g, 19.64 mmol) was added, and the reaction solution was stirred at 25° C. for 2 hours. TLC (petroleum ether:ethyl acetate=3:1) showed that compound 1-e was reacted completely and a new product was formed. The reaction solution was concentrated under reduced pressure to remove excess dichloromethane. The obtained crude product was purified by silica gel column chromatography (petroleum ether/ethyl acetate=3/1) to obtain compound 1-g. $^1$H NMR (400 MHz, $CDCl_3$): 8.21 (d, J=0.6 Hz, 1H), 7.52 (d, J=15.9 Hz, 1H), 6.32 (d, J=15.8 Hz, 1H), 5.06 (br d, J=5.1 Hz, 1H), 4.32-4.29 (m, 2H), 2.55 (s, 3H), 2.31-2.21 (m, 1H), 2.07-1.97 (m, 1H), 1.93-1.71 (m, 3H), 1.64-1.52 (m, 1H), 1.37 (t, J=7.1 Hz, 3H), 1.14 (s, 3H).

Synthesis of Compound 1-h

Compound 1-g (560 mg, 1.66 mmol) was added to tetrahydrofuran (10 mL), then $(PPh_3)_3RhCl$ (307.09 mg, 331.91 μmol) was added under nitrogen protection, the reaction solution was purged with hydrogen several times, the reaction solution was stirred at 50° C. for 16 hours under hydrogen pressure 50 Psi. LCMS showed the reaction was complete. The reaction solution was cooled to 25° C., concentrated under reduced pressure, and the obtained crude product was purified by silica gel column chromatography (petroleum ether/ethyl acetate=3/1) to obtain compound 1-h. $^1$H NMR (400 MHz, $CDCl_3$): 7.74 (s, 1H), 5.73 (br d, J=4.3 Hz, 1H), 5.46 (s, 1H), 4.19-4.12 (m, 1H), 2.66-2.59 (m, 2H), 2.55-2.48 (m, 2H), 2.42 (s, 3H), 2.17-2.07 (m, 1H), 1.96-1.87 (m, 1H), 1.81-1.70 (m, 2H), 1.57-1.47 (m, 2H), 1.21-1.18 (m, 3H), 1.01 (s, 3H).

Synthesis of Compound 1-i

Compound 1-h (360 mg, 1.06 mmol) was added to N-methylpyrrolidone (5 mL), followed by DBU (322.90 mg, 2.12 mmol, 319.71 μL), and the reaction solution was stirred at 120° C. for 16 hours. LCMS showed the reaction was complete. The reaction solution was cooled to 25° C., extracted with ethyl acetate (10 mL×3), the organic phases were combined, washed with saturated brine (20 mL), dried over anhydrous sodium sulfate, and filtered, the filtrate was concentrated, and the obtained crude product was purified by silica gel column chromatography (petroleum ether/ethyl acetate=1/1) to obtain compound 1-i. LCMS (ESI):m/z: 294.2 (M+1); $^1$H NMR (400 MHz, $CDCl_3$): 8.23 (s, 1H), 5.00 (t, J=8.8 Hz, 1H), 2.88-2.81 (m, 2H), 2.75-2.65 (m, 4H), 2.57 (s, 3H), 2.05-1.90 (m, 4H), 1.19 (s, 3H).

Synthesis of Compound 1-j

Compound 1-i (100 mg, 340.85 μmol) was added to 2-methyltetrahydrofuran (1 mL) and water (0.2 mL), followed by potassium hydrogen persulfate complex salt (523.86 mg, 852.13 μmol), and stirred at 25° C. for 2 hours. LCMS showed the reaction was complete. The reaction solution was quenched with saturated sodium sulfite (15 mL), extracted with ethyl acetate (10 mL×3), the organic phases were combined, washed with saturated brine (15 mL), dried over anhydrous sodium sulfate, and filtered, the filtrate was concentrated to obtain compound 1-j. LCMS (ESI):m/z: 307.8 (M−18+1);

$^1H$ NMR (400 MHz, $CDCl_3$): 8.45 (s, 1H), 5.01 (t, J=8.7 Hz, 1H), 3.25 (s, 3H), 2.96-2.91 (m, 2H), 2.76-2.69 (m, 2H), 2.12-1.98 (m, 2H), 1.96-1.88 (m, 2H), 1.84-1.78 (m, 2H), 1.09 (s, 3H).

Synthesis of Compound 1

Compound 1-j (80 mg, 245.86 μmol) was added to dimethyl sulfoxide (1 mL), followed by 1-k (79.19 mg, 368.80 μmol, hydrochloride) and diisopropylethylamine (158.88 mg, 1.23 mmol, 214.13 μL), the reaction mixture was stirred at 120° C. for 16 hours. LCMS showed the reaction was complete. The reaction solution was cooled to 25° C., added with water (10 mL), and extracted with ethyl acetate (10 mL×3), the organic phases were combined, washed with saturated brine (15 mL×2), dried over anhydrous sodium sulfate, and filtered, the filtrate was concentrated, and the crude product was purified by preparative chromatography (chromatographic column: 3_Phenomenex Luna C18 75×30 mm×3 μm; mobile phase: 0.05% hydrochloric acid solution as mobile phase A, acetonitrile as mobile phase B, B %: 11%-31%, gradient time: 6.5 min). The pH of the purified mixed solution was adjusted to 7~8 with saturated sodium bicarbonate, then extracted with dichloromethane (10 mL×3), the organic phases were combined, washed with saturated brine (15 mL×2), dried over anhydrous sodium sulfate, and filtered, the filtrate was evaporated to dryness to obtain compound 1. LCMS (ESI) m/z: 424.1 (M+1).

Synthesis of Compound 1B

Compound 1 was chirally separated by SFC to obtain 1A and 1B.

Compound 1 was prepared by SFC (column: polyoxymethylene-coated chiral stationary phase (250 mm×30 mm×10 μm); mobile phase: 45% [0.1% ammonia ethanol solution]; purified to obtain compound 1A (retention time 0.548 minute) and compound 1B (retention time 0.895 minute).

Compound 1B: $^1H$ NMR (400 MHz, MeOD) δ 7.87 (s, 1H), 5.17 (br t, J=8.6 Hz, 1H), 3.85-3.76 (m, 1H), 3.64-3.55 (m, 2H), 2.89-2.81 (m, 2H), 2.76 (s, 3H), 2.66-2.59 (m, 2H), 2.54-2.48 (m, 2H), 2.40-2.31 (m, 1H), 2.12-1.92 (m, 4H), 1.82-1.73 (m, 2H), 1.67-1.60 (m, 1H), 1.57-1.46 (m, 2H), 1.06 (s, 3H).

Example 2: the Hydrochloride Salt of Compound 2

2

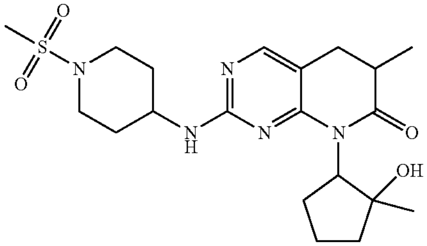

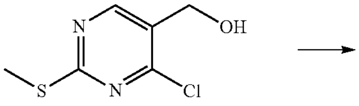

1-b

-continued

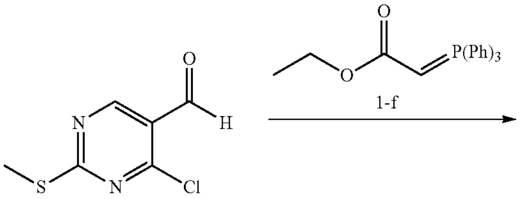

2-a

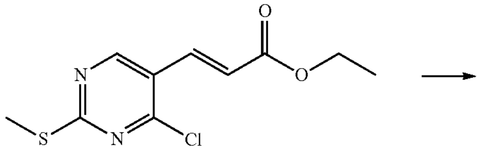

2-b

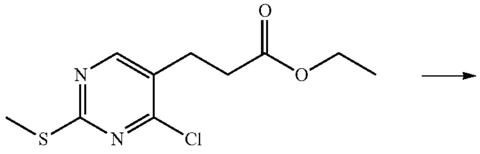

2-c

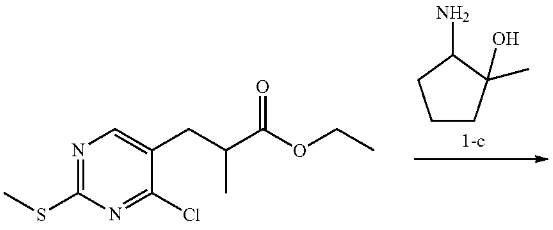

2-d

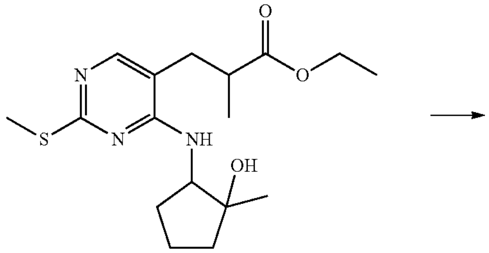

2-e

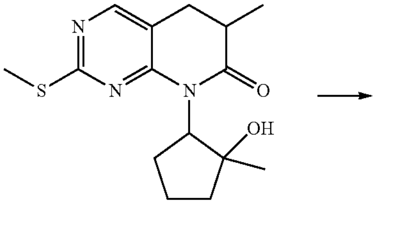

2-f

-continued

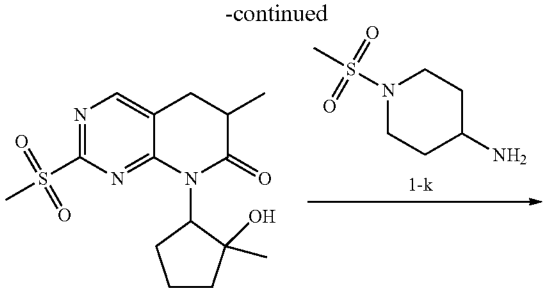

2-g

The hydrochlorid salt of Compound 2;

Synthesis of Compound 2-a

Compound 1-b (5 g, 26.23 mmol) was added to ethyl acetate (50 mL), then active manganese dioxide (22.80 g, 262.26 mmol) was added, and the reaction solution was stirred at 50° C. for 16 hours. TLC (petroleum ether:ethyl acetate=3:1) showed that compound 1-b was reacted completely and a new product was formed. The reaction solution was cooled to 25° C. and filtered, the filter cake was washed with methanol (30 mL×3), the filtrate was evaporated to dryness, and the obtained crude product was purified by silica gel column chromatography (petroleum ether/ethyl acetate=3/1) to obtain compound 2-a. $^1$H NMR (400 MHz, $CDCl_3$): δ 10.33 (s, 1H), 8.89 (s, 1H), 2.66 (s, 3H).

Synthesis of Compound 2-b

Compound 2-a (3 g, 15.90 mmol) was added to dichloromethane (20 mL), followed by compound 1-f (5.82 g, 16.70 mmol), and the reaction solution was stirred at 30° C. for 2 hours. TLC (petroleum ether:ethyl acetate=10:1) showed that compound 2-a was reacted completely and a new product was formed. The reaction solution was concentrated under reduced pressure, and the obtained crude product was purified by silica gel column chromatography (petroleum ether/ethyl acetate=3/1) to obtain compound 2-b.

$^1$H NMR (400 MHz, $CDCl_3$): δ 8.66 (s, 1H), 7.81 (d, J=16.1 Hz, 1H), 6.51 (d, J=16.3 Hz, 1H), 4.31 (q, J=7.2 Hz, 2H), 2.61 (s, 3H), 1.37 (t, J=7.1 Hz, 3H).

Synthesis of Compound 2-c

Compound 2-b (4.2 g, 16.23 mmol) was added to 2-methyltetrahydrofuran (20 mL), then $Rh(PPh_3)_3Cl$ (3.00 g, 3.25 mmol) was added, the reaction solution was purged with hydrogen several times, the reaction solution was stirred at 80° C. for 16 hours. LCMS showed the reaction was complete. The reaction solution was cooled to 20° C., concentrated under reduced pressure to remove excess 2-methyltetrahydrofuran, and the obtained crude product was purified by silica gel column chromatography (petroleum ether/ethyl acetate=10/1) to obtain compound 2-c. LCMS (ESI): m/z: 260.9 (M+1).

Synthesis of Compound 2-d

Compound 2-c (1.9 g, 7.29 mmol) was added to tetrahydrofuran (20 mL), cooled to −78° C., lithium diisopropylamide (1 M, 18.22 mL) was slowly added under nitrogen protection, the reaction solution was stirred at −78° C. for 30 minutes, then iodomethane (1.55 g, 10.93 mmol, 680.46 μL) was added, and the reaction solution was warmed to 25° C. and stirred for 1.5 hours. TLC (petroleum ether:ethyl acetate=10:1) showed that the reaction of compound 2-c was complete and a new product was formed. The reaction solution was quenched with saturated ammonium chloride (25 mL), extracted with ethyl acetate (10 mL×3), the combined organic phases were washed with saturated brine (20 mL), dried over anhydrous sodium sulfate, filtered, and the filtrate was evaporated to dryness, the obtained crude product was purified by silica gel column chromatography (petroleum ether/ethyl acetate=10/1) to obtain compound 2-d.

Synthesis of Compound 2-e

Compound 2-d (1.2 g, 4.37 mmol) and compound 1-c (1.01 g, 8.73 mmol) were added to dimethyl sulfoxide (20 mL), followed by diisopropylethylamine (1.69 g, 13.10 mmol, 2.28 mL), the reaction solution was stirred at 110° C. for 16 hours. LCMS showed the reaction was complete. The reaction solution was cooled to 25° C., added with water (5 mL), and washed with ethyl acetate (10 mL×3), the organic phases were combined, washed with saturated brine (20 mL), dried over anhydrous sodium sulfate, filtered, and the filtrate was evaporation to dryness, the obtained crude product was purified by silica gel column chromatography (petroleum ether/ethyl acetate=3/1) to obtain compound 2-e. LCMS (ESI): m/z: 354.2 (M+1); $^1$H NMR (400 MHz, $CDCl_3$): 7.84-7.81 (m, 1H), 4.17-4.11 (m, 2H), 2.80 (td, J=8.0, 15.0 Hz, 1H), 2.66-2.59 (m, 1H), 2.51 (d, J=0.6 Hz, 3H), 2.49-2.41 (m, 1H), 2.28-2.17 (m, 1H), 2.00 (dt, J=3.5, 7.5 Hz, 1H), 1.90-1.81 (m, 2H), 1.79-1.68 (m, 1H), 1.61 (s, 5H), 1.27-1.25 (m, 3H), 1.11 (d, J=8.2 Hz, 3H).

Synthesis of Compound 2-f

Compound 2-e (1.1 g, 3.11 mmol) was added to N-methylpyrrolidone (15 mL), then DBU (947.50 mg, 6.22 mmol, 938.12 μL) was added, and the reaction solution was stirred at 120° C. for 12 hours. LCMS showed the reaction was complete. The reaction solution was cooled to 25° C., added with water (20 mL), washed with ethyl acetate (20 mL×3), the organic phases were combined, washed with saturated brine (30 mL×2), dried over anhydrous sodium sulfate, and filtered, the filtrate was evaporated to dryness, and the obtained crude product was purified by silica gel column chromatography (petroleum ether/ethyl acetate=2/1) to obtain compound 2-f LCMS (ESI): m/z: 208.2 (M+1).

Synthesis of Compound 2-g

Compound 2-f (1 g, 3.25 mmol) was added to 2-methyltetrahydrofuran (10 mL) and water (2 mL), then potassium hydrogen persulfate double salt (5.00 g, 8.13 mmol) was added, and the reaction solution was stirred at 25° C. for 2 hours. LCMS showed the reaction was complete. The reaction solution was quenched with saturated sodium sulfite (50 mL), extracted with ethyl acetate (20 mL×3), the organic phases were combined, washed with saturated brine (30 mL×3), dried over anhydrous sodium sulfate, and filtered, the filtrate was concentration to obtain compound 2-g. LCMS (ESI): m/z: 322.1 (M−18+1); $^1$H NMR (400 MHz, $CDCl_3$): 8.46-8.42 (m, 1H), 3.31 (t, J=7.1 Hz, 2H), 3.25 (s, 3H), 3.00 (dt, J=4.5, 14.1 Hz, 1H), 2.77 (s, 3H), 2.28-2.28

(m, 1H), 2.30 (t, J=8.1 Hz, 1H), 1.81-1.77 (m, 1H), 1.27-1.19 (m, 4H), 1.10-1.06 (m, 3H).

Synthesis of Compound 2

Compound 2-g (500 mg, 1.47 mmol) and compound 1-k (474.46 mg, 2.21 mmol, hydrochloride) were added to dimethyl sulfoxide (8 mL), followed by diisopropylethylamine (951.95 mg, 7.37 mmol, 1.28 mL), the reaction solution was stirred at 140° C. for 16 hours. LCMS showed the reaction was complete. The reaction solution was cooled to 25° C., added with water (20 mL), washed with ethyl acetate (10 mL×3), the organic phases were combined, washed with saturated brine (15 mL×2), dried over anhydrous sodium sulfate, and filtered, the filtrate was evaporated to dryness, and the obtained crude product was purified by preparative chromatography (chromatographic column: 3_Phenomenex Luna C18 75×30 mm×3 μm; mobile phase: 0.05% hydrochloric acid solution as mobile phase A, acetonitrile as mobile phase B, B %: 13%-33%, gradient time: 6.5 min) to obtain the hydrochloride salt of compound 2.

LCMS (ESI): m/z: 438.1 (M+1); $^1$H NMR (400 MHz, MeOD) δ 8.01 (d, J=2.4 Hz, 1H), 3.83-3.75 (m, 1H), 3.09-2.93 (m, 4H), 2.90 (s, 3H), 2.78-2.57 (m, 2H), 2.53-2.25 (m, 2H), 2.25-2.10 (m, 4H), 1.97-1.89 (m, 2H), 1.82-1.67 (m, 4H), 1.28 (dd, J=6.7, 11.4 Hz, 3H), 1.17 (d, J=2.4 Hz, 3H).

Example 3: Compound 3

3

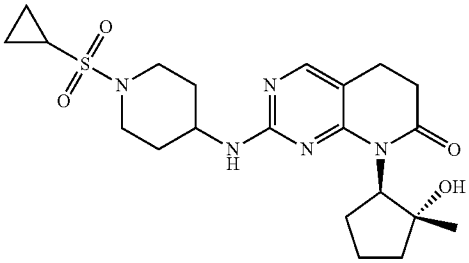

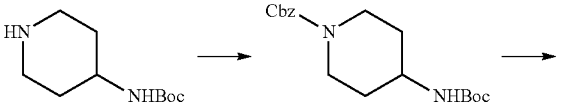

3-a 3-b

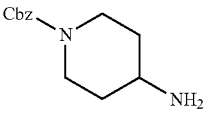

3-c

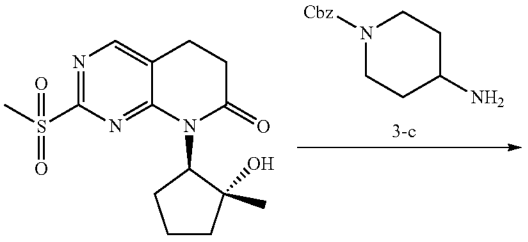

3-c 3-d

-continued

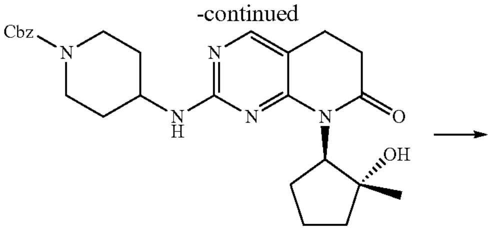

3-e

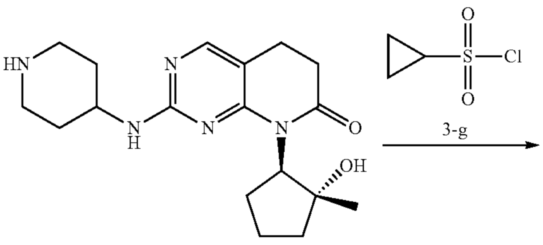

3-f

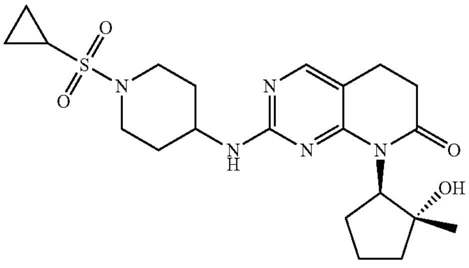

3

Synthesis of Compound 3-b

Compound 3-a (5 g, 24.97 mmol) and triethylamine (5.05 g, 49.93 mmol) were dissolved in dichloromethane (50 mL), then the resulting mixture was stirred at 15° C. for 0.5 h under nitrogen protection, then benzyl chloroformate (6.39 g, 37.45 mmol) was slowly added and the resulting mixture was stirred at this temperature for 1.5 hours. The reaction solution was diluted with water (80 mL), and extracted with dichloromethane (30 mL×4). The obtained organic phase was washed with saturated brine (60 mL×1), dried over anhydrous $Na_2SO_4$, filtered and concentrated. The obtained crude product was purified by stirring with petroleum ether (50 mL) at 25° C. for 3 hours to obtain compound 3-b. $^1$H NMR (400 MHz, $CD_3OD$) δ ppm 1.24-1.37 (m, 2H) 1.43 (s, 9H) 1.83 (br d, J=10.51 Hz, 2H) 2.95 (br s, 2H) 3.44-3.57 (m, 1H) 4.05 (br d, J=13.51 Hz, 2H) 5.10 (s, 2H) 7.23-7.40 (m, 5H); LCMS (ESI):m/z: 335.2 (M+1).

Synthesis of Compound 3-c

Compound 3-b (7 g, 20.93 mmol) was dissolved in ethyl acetate (100 mL), then HCl-ethyl acetate solution (4 M, 52.33 mL) was added, the resulting mixture was stirred at 15° C. for 2 hours, and the reaction solution was concentrated to obtain compound 3-c. $^1$H NMR (400 MHz, $CD_3OD$) δ ppm 1.49 (qd, J=12.29, 4.46 Hz, 2H) 2.00 (br d, J=12.35 Hz, 2H) 2.94 (br s, 2H) 3.34 (s, 2H) 4.22 (dt, J=13.97, 2.25 Hz, 2H) 5.12 (s, 2H) 7.27-7.38 (m, 5H); LCMS (ESI):m/z: 235.2 (M+1).

Synthesis of Compound 3-e

Compound 3-d (1.2 g, 3.69 mmol), compound 3-c (2.59 g, 11.06 mmol) and diisopropylethylamine (3.81 g, 29.50 mmol) were dissolved in dimethyl sulfoxide (20 mL), the resulting mixture was stirred at 110° C. for 12 hours, the reaction solution was diluted with water (100 mL), and extracted with ethyl acetate (60 mL×3). The obtained organic phase was washed with saturated brine (100 mL×1), dried over anhydrous $Na_2SO_4$, filtered and concentrated. The obtained crude compound was purified by thin layer chromatography (dichloromethane:methanol=10:1) to obtain compound 3-e. LCMS (ESI):m/z: 480.3 (M+1).

Synthesis of Compound 3-f

Compound 3-e (830 mg, 1.73 mmol) and wet palladium carbon (300 mg, 10%) were dissolved in methanol (15 mL), and the resulting mixture was stirred at 15° C. for 2 hours under 15 psi hydrogen, and the reaction solution was filtered, the filtrate was concentrated to obtain compound 3-f.

Synthesis of Compound 3

Compound 3-f (100 mg, 289.49 μmol), 3-g (61.05 mg, 434.23 μmol) and triethylamine (43.94 mg, 434.23 μmol) were dissolved in dichloromethane (2 mL), and the resulting mixture was stirred at 15° C. for 1 hour. The reaction solution was concentrated, and purified by preparative chromatography (chromatographic column: Waters Xbridge 150×25 mm×5 μm; mobile phase: 10 mM ammonium bicarbonate solution as mobile phase A, acetonitrile as mobile phase B, B %: 20%-50%, gradient time: 9 min) to obtain compound 3. $^1H$ NMR (400 MHz, $CD_3OD$) δ ppm 1.01-1.07 (m, 4H) 1.16 (s, 3H) 1.53-1.66 (m, 2H) 1.68-1.77 (m, 1H) 1.83-1.92 (m, 2H) 2.00-2.20 (m, 4H) 2.42-2.53 (m, 2H) 2.56-2.64 (m, 2H) 2.68-2.78 (m, 2H) 3.07 (td, J=12.10, 2.08 Hz, 2H) 3.74 (br dd, J=12.23, 3.55 Hz, 2H) 3.86-3.98 (m, 1H) 5.27 (br t, J=8.44 Hz, 1H) 7.97 (s, 1H) LCMS (ESI): m/z: 450.3 (M+1).

Example 4: Compound 4

4

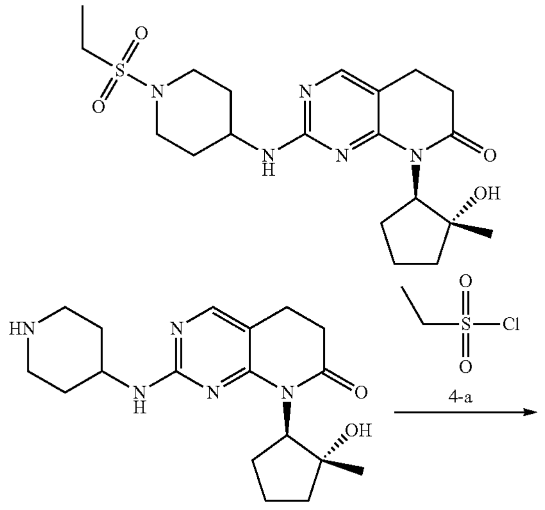

3-f

-continued

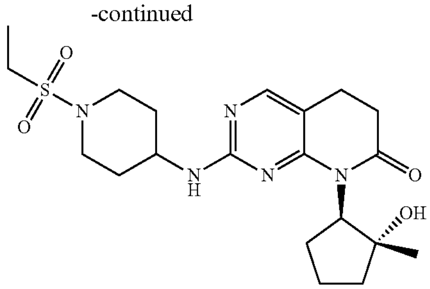

4

Synthesis of Compound 4

Compound 3-f (100 mg, 289.49 μmol), 4-a (55.83 mg, 434.23 μmol) and triethylamine (43.94 mg, 434.23 μmol) were dissolved in dichloromethane (2 mL), and the resulting mixture was stirred at 15° C. for 1 hour. The reaction solution was concentrated, and was purified by preparative chromatography (chromatographic column: Waters Xbridge 150×25 mm×5 μm; mobile phase: 10 mM ammonium bicarbonate solution as mobile phase A, acetonitrile as mobile phase B, B %: 15%-48%, gradient time: 10 min) to obtain compound 4. $^1H$ NMR (400 MHz, $CD_3OD-d_4$) δ ppm 1.17 (s, 3H) 1.34 (t, J=7.40 Hz, 3H) 1.52-1.65 (m, 2H) 1.69-1.77 (m, 1H) 1.83-1.94 (m, 2H) 2.00-2.22 (m, 4H) 2.42-2.52 (m, 1H) 2.56-2.67 (m, 2H) 2.68-2.77 (m, 2H) 3.00-3.09 (m, 4H) 3.70-3.78 (m, 2H) 3.86-3.97 (m, 1H) 5.2.7 (br t, J=8.62 Hz, 1H) 7.98 (s, 1H); LCMS (ESI):m/z: 438.3 (M+1).

Example 5: Compound 5

5

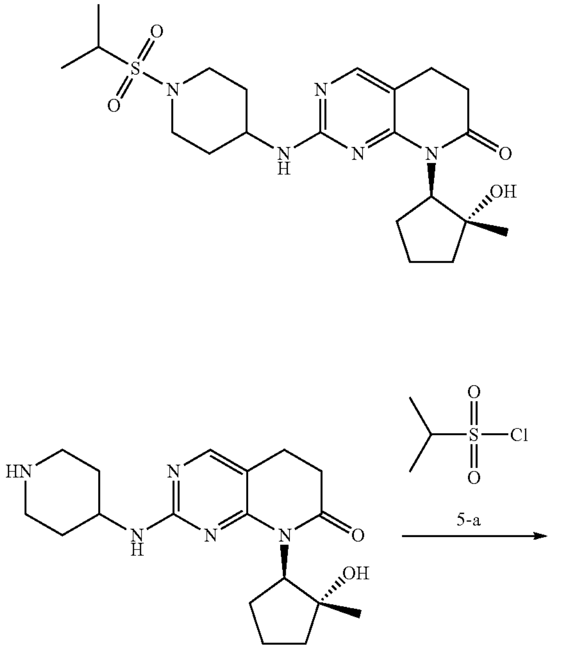

3-f

-continued

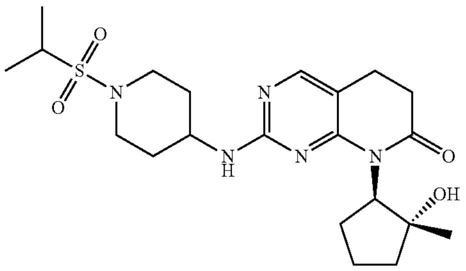

5

Synthesis of Compound 5

Compound 3-f (100 mg, 289.49 μmol), 5-a (61.92 mg, 434.23 μmol) and triethylamine (43.94 mg, 434.23 μmol) were dissolved in dichloromethane (2 mL), and the resulting mixture was stirred at 15° C. for 1 hour. The reaction solution was concentrated, and was purified by preparative chromatography (chromatographic column: Waters Xbridge 150×25 mm×5 μm; mobile phase: 10 mM ammonium bicarbonate solution as mobile phase A, acetonitrile as mobile phase B, B %: 21%-51%, gradient time: 9 min) to obtain compound 5. $^1$H NMR (400 MHz, METHANOL-$d_4$) δ ppm 1.16 (s, 3H) 1.32 (d, J=6.72 Hz, 6H) 1.49-1.60 (m, 2H) 1.69-1.76 (m, 1H) 1.83-1.93 (m, 2H) 1.98-2.11 (m, 3H) 2.17 (td, J=11.80, 8.07 Hz, 1H) 2.41-2.52 (m, 1H) 2.57-2.64 (m, 2H) 2.67-2.76 (m, 2H) 3.10 (br t, J=11.37 Hz, 2H) 3.73-3.82 (m, 2H) 3.86-3.98 (m, 1H) 5.26 (br t, J=8.56 Hz, 1H) 7.96 (s, 1H); LCMS (ESI):m/z: 452.3 (M+1).

Example 6: Compound 6

6

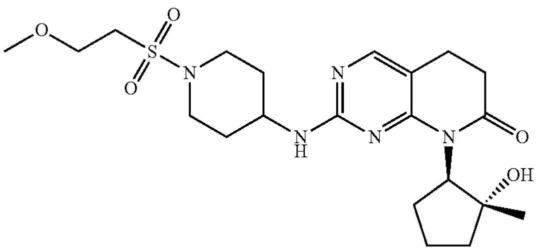

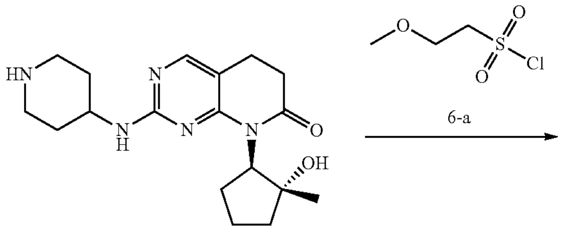

3-f 6-a

-continued

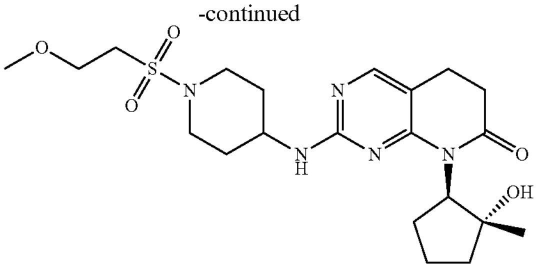

6

Synthesis of Compound 6

Compound 6-a (2.30 mg, 14.47 μmol) was added dropwise to a solution of compound 3-f (5 mg, 14.47 μmol) and triethylamine (2.93 mg, 28.95 μmol, 4.03 μmL) in dichloromethane (1 mL) at 0° C., and the reaction solution was stirred at 15° C. for 2 hours. LC-MS showed that the starting material was reacted completely and formation of the target product was detected. The reaction solution was concentrated under reduced pressure, and was purified by preparative chromatography (chromatographic column: Waters Xbridge 150×25 mm×5 μm; mobile phase: 0.05% aqueous ammonia solution as mobile phase A, acetonitrile as mobile phase B, B %: 18%-48%, gradient time: 9 min) to obtain compound 6. $^1$H NMR (400 MHz, $CD_3OD$) δ 7.87 (s, 1H), 5.17 (br s, 1H), 3.84-3.73 (m, 1H), 3.68-3.56 (m, 4H), 3.28 (s, 3H), 3.20-3.15 (m, 2H), 2.92 (br t, J=11.3 Hz, 2H), 2.67-2.57 (m, 2H), 2.55-2.47 (m, 2H), 2.43-2.31 (m, 1H), 2.13-1.89 (m, 4H), 1.84-1.74 (m, 2H), 1.66-1.59 (m, 1H), 1.55-1.40 (m, 2H), 1.24-1.17 (m, 1H), 1.10-1.02 (m, 3H). LCMS (ESI) m/z: 468.4 (M+1).

Example 7: Compound 7

7

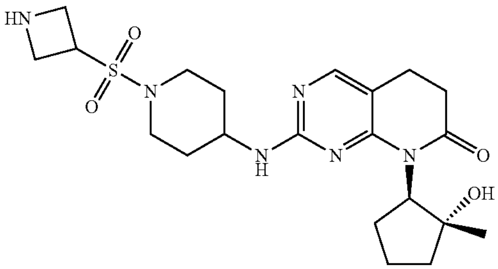

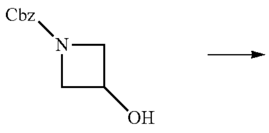

7-a

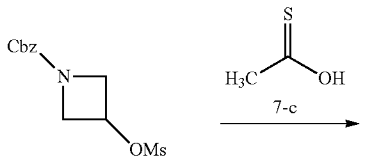

7-b 7-c

-continued

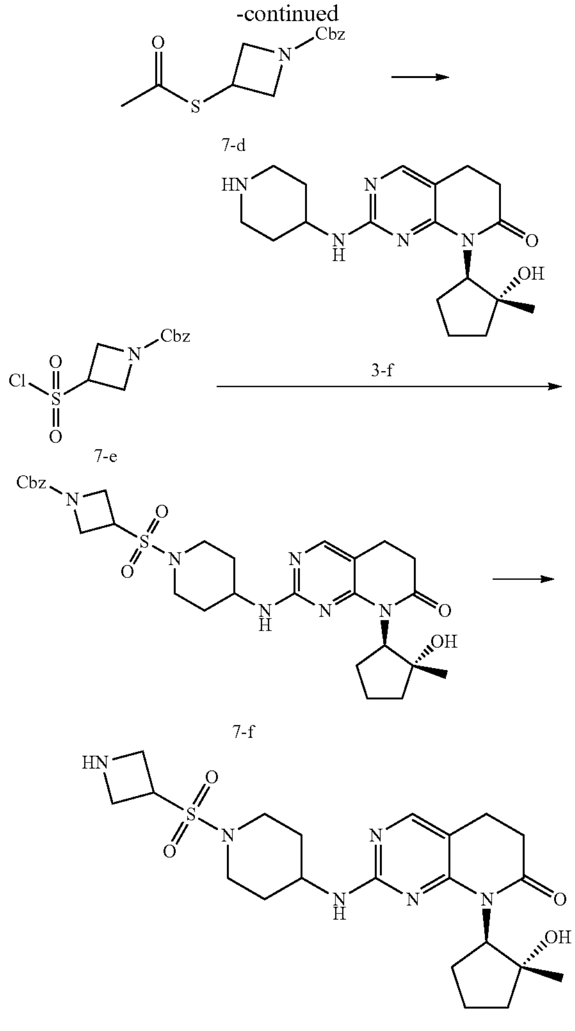

7-d 3-f 7-e 7-f

7

Synthesis of Compound 7-b

Compound 7-a (7.5 g, 36.19 mmol) and triethylamine (5.49 g, 54.29 mmol, 7.56 mL) were added to dichloromethane (100 mL), cooled to 0° C., and then methanesulfonyl chloride (4.98 g, 43.43 mmol, 3.36 mL) was added dropwise to the reaction solution, the reaction temperature was raised to 15° C., and the reaction was stirred for 3 hours. TLC (petroleum ether/ethyl acetate=1/1) showed that the reaction was complete and new compounds were formed. The reaction solution was quenched with 1 M hydrochloric acid solution (50 mL) and extracted with dichloromethane (50 mL×3), the organic phases were combined, washed with saturated brine (100 mL), dried over anhydrous sodium sulfate, filtered, and the filtrate was evaporated to dryness to obtain compound 7-b. $^1H$ NMR (400 MHz, $CDCl_3$): δ 7.32-7.23 (m, 5H), 5.16 (tt, J=4.2, 6.7 Hz, 1H), 5.03 (s, 2H), 4.32-4.26 (m, 2H), 4.13-4.08 (m, 2H), 2.99 (s, 3H).

Synthesis of Compound 7-d

Compound 7-b (5 g, 17.52 mmol) was added to N,N-dimethylformamide (50 mL), potassium carbonate (3.63 g, 26.29 mmol) was added, the reaction solution was cooled to 0° C., and then compound 7-c (2.00 g, 26.29 mmol) was added dropwise. The reaction solution was heated to 80° C. and stirred for 16 hours. LCMS showed the reaction was complete. The reaction solution was cooled to 20° C., added with water (100 mL), and extracted with ethyl acetate (50 mL×3), the organic phases were combined, washed with saturated brine (100), dried over anhydrous sodium sulfate, and filtered, the filtrate was evaporated to dryness, the obtained crude product was purified by silica gel column chromatography (petroleum ether/ethyl acetate=5/1) to obtain compound 7-d. $^1H$ NMR (400 MHz, $CDCl_3$): δ 7.41-7.30 (m, 5H), 5.12 (s, 2H), 4.48 (t, J=8.8 Hz, 2H), 4.23 (tt, J=5.6, 8.2 Hz, 1H), 3.92 (dd, J=5.6, 9.5 Hz, 2H), 2.35 (s, 3H); LCMS (ESI): m/z: 266.0 (M+1).

Synthesis of Compound 7-e

Compound 7-d (2.5 g, 9.42 mmol) was added to water (10 mL) and dichloromethane (20 mL), cooled to 0° C., then chlorine gas was passed into the reaction system, and the reaction solution was reacted with chlorine gas at 0-10° C. for 1 hour. TLC (petroleum ether/ethyl acetate=5/1) showed that the reaction was complete and new compounds were formed. The reaction solution was separated, the organic phase was washed with water (50 mL), saturated sodium carbonate (50 mL×1) and saturated brine (50 mL×1), dried over anhydrous sodium sulfate, and filtered, the filtrate was evaporated to dryness, the obtained crude product was purified by silica gel column chromatography (petroleum ether/ethyl acetate=5/1) to obtain compound 7-e. $^1H$ NMR (400 MHz, $CDCl_3$): δ 7.31-7.26 (m, 5H), 5.06 (s, 2H), 4.55-4.34 (m, 5H).

Synthesis of Compound 7-f

Compound 3-f (1 g, 2.89 mmol) and triethylamine (585.86 mg, 5.79 mmol, 805.86 μL) were added to dichloromethane (10 mL), followed by compound 7-e (838.75 mg, 2.89 mmol), the reaction solution was stirred at 15° C. for 16 hours. LCMS showed the reaction was complete. The reaction solution was evaporated to dryness under reduced pressure, and the obtained crude product was purified by silica gel column chromatography (petroleum ether/ethyl acetate=0/1) to obtain compound 7-f. $^1H$ NMR (400 MHz, $CD_3OD$): δ 7.98 (s, 1H), 7.38-7.29 (m, 5H), 5.28 (br t, J=8.5 Hz, 1H), 5.14-5.13 (m, 2H), 4.34-4.22 (m, 5H), 3.95-3.89 (m, 1H), 3.81-3.75 (m, 2H), 3.10-3.02 (m, 2H), 2.99-2.88 (m, 1H), 2.77-2.71 (m, 2H), 2.65-2.59 (m, 2H), 2.51-2.43 (m, 1H), 2.24-2.16 (m, 1H), 1.95-1.86 (m, 3H), 1.82-1.72 (m, 2H), 1.61-1.51 (m, 2H), 1.17 (s, 3H); LCMS (ESI): m/z: 599.4 (M+1).

Synthesis of Compound 7

Compound 7-f (1.1 g, 1.84 mmol) was added to methanol (20 mL), wet palladium/carbon (10%, 200 mg) was added under nitrogen protection, and the reaction solution was purged with hydrogen several times. The reaction was stirred at 15° C. for 10 hours under hydrogen (15 psi). LCMS showed the reaction was complete. The reaction solution was filtered through diatomite, the filtrate was evaporated to dryness, and the obtained crude product was purified by preparative chromatography (chromatographic column: Waters Xbridge C18 250×50 mm×10 μm; mobile phase: 0.05% aqueous ammonia solution as mobile phase A, and acetonitrile as mobile phase B, B %: 15%-30%, gradient time: 20 min) to obtain compound 7. $^1H$ NMR (400 MHz, $CDCl_3$): δ 7.98 (s, 1H), 5.28 (br t, J=8.4 Hz, 1H), 4.39 (quin, J=7.6 Hz, 1H), 4.02-3.70 (m, 7H), 3.02 (br t, J=11.6 Hz, 2H), 2.77-2.70 (m, 2H), 2.66-2.59 (m, 2H), 2.51-2.41 (m, 1H), 2.23-2.03 (m, 4H), 1.94-1.86 (m, 2H), 1.78-1.73 (m, 1H), 1.55 (dq, J=8.1, 11.6 Hz, 2H), 1.18 (s, 3H); LCMS (ESI): m/z: 465.3 (M+1).

Example 8: Compound 8

8

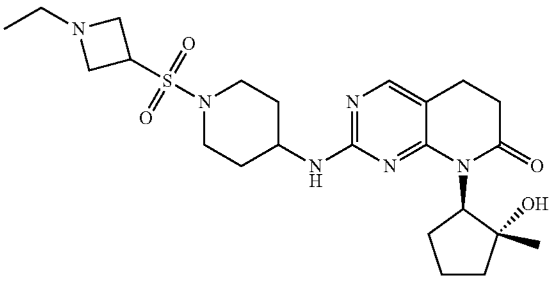

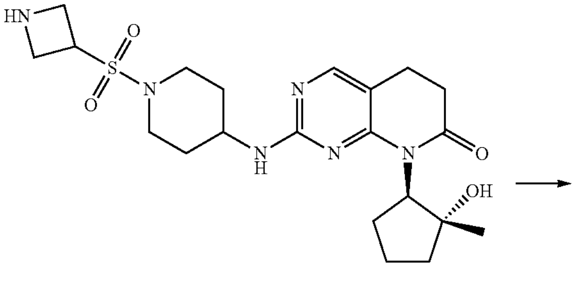

7

8

Synthesis of Compound 8

Compound 7 (70 mg, 145.05 μmol) and acetaldehyde (31.95 mg, 725.27 μmol, 40.70 μL) were added to methanol (2 mL), stirred at 15° C. for 30 minutes, then added with sodium cyanoborohydride (18.23 mg, 290.11 μmol), and stirred at 15° C. for 1 hour. LCMS showed the reaction was complete. The reaction solution was evaporated to dryness under reduced pressure, and the obtained crude product was purified by preparative chromatography (chromatographic column: Waters Xbridge C18 150×25 mm×5 μm; mobile phase: 10 mM ammonium bicarbonate solution as mobile phase A, acetonitrile as mobile phase B, B %: 18%-48%, gradient time: 9 min) to obtain compound 8. $^1H$ NMR (400 MHz, $CD_3OD$): δ 7.98 (s, 1H), 5.28 (br t, J=8.5 Hz, 1H), 4.15 (quin, J=7.6 Hz, 1H), 3.95-3.88 (m, 1H), 3.74 (br dd, J=3.7, 12.4 Hz, 2H), 3.68 (t, J=8.5 Hz, 2H), 3.46 (t, J=8.1 Hz, 2H), 3.02 (br t, J=11.7 Hz, 2H), 2.77-2.71 (m, 2H), 2.65-2.56 (m, 4H), 2.53-2.43 (m, 1H), 2.24-2.04 (m, 4H), 1.95-1.86 (m, 2H), 1.79-1.72 (m, 1H), 1.62-1.49 (m, 2H), 1.18 (s, 3H), 1.00 (t, J=7.2 Hz, 3H); LCMS (ESI): m/z: 493.4 (M+1).

Example 9: Compound 9

9

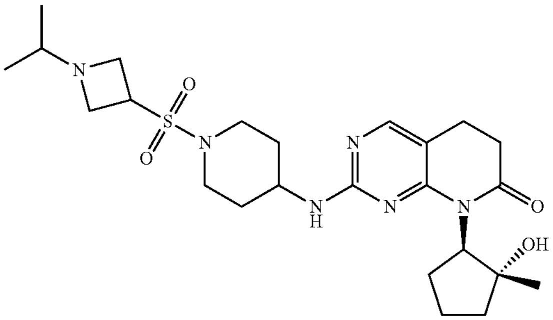

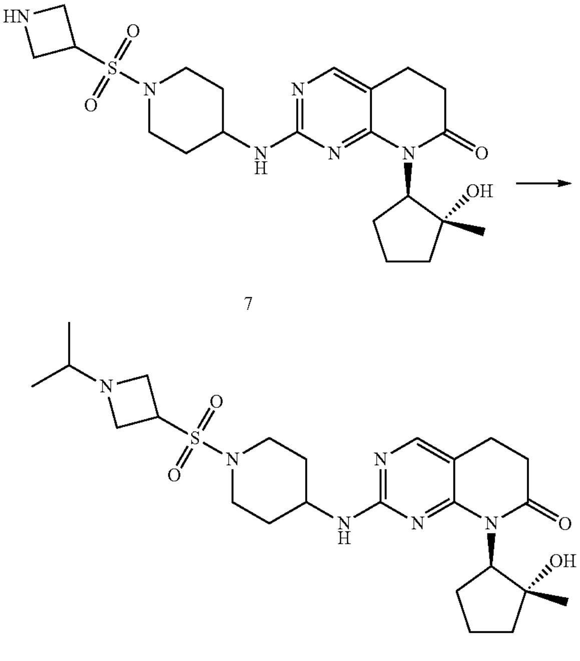

7

9

Synthesis of Compound 9

Compound 7 (70 mg, 145.05 μmol) and acetone (42.12 mg, 725.25 μmol, 53.32 μL) were added to methanol (2 mL), stirred at 15° C. for 30 minutes, then added with sodium cyanoborohydride (18.23 mg, 290.11 μmol), and stirred at 15° C. for 1 hour. LCMS showed the reaction was complete. The reaction solution was evaporated to dryness under reduced pressure, and the obtained crude product was purified by preparative chromatography (chromatographic column: Waters Xbridge C18 150×25 mm×5 μm; mobile phase: 10 mM ammonium bicarbonate solution as mobile phase A, acetonitrile as mobile phase B, B %: 22%-52%, gradient time: 9 min) to obtain compound 9. $^1H$ NMR (400 MHz, $CD_3OD$): δ 7.98 (s, 1H), 5.28 (br t, J=8.6 Hz, 1H), 4.08 (quin, J=7.7 Hz, 1H), 3.97-3.87 (m, 1H), 3.74 (br dd, J=3.8, 12.3 Hz, 2H), 3.67 (t, J=8.4 Hz, 2H), 3.46 (t, J=8.2 Hz, 2H), 3.03 (br t, J=11.7 Hz, 2H), 2.79-2.70 (m, 2H), 2.67-2.58 (m, 2H), 2.55-2.43 (m, 2H), 2.24-2.03 (m, 4H), 1.94-1.84 (m, 2H), 1.79-1.72 (m, 1H), 1.62-1.49 (m, 2H), 1.18 (s, 3H), 0.97 (d, J=6.2 Hz, 6H); LCMS (ESI): m/z: 507.4 (M+1).

Example 10: Compound 10

10

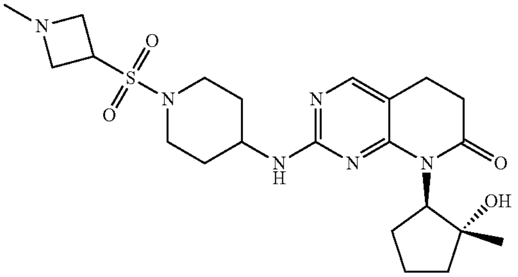

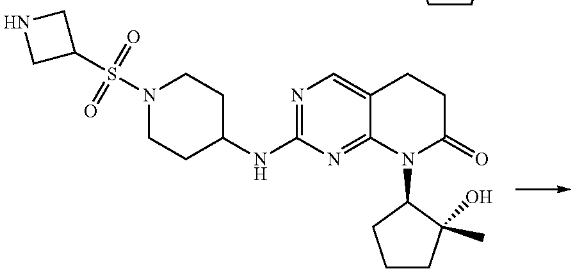

7

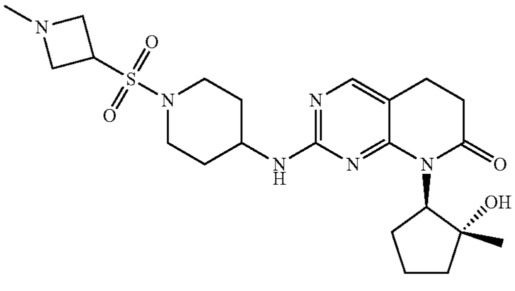

10

Synthesis of Compound 10

Compound 7 (90 mg, 145.05 μmol) and formaldehyde (75.67 mg, 932.49 μmol, 69.42 μL, 37% purity) were added to methanol (2 mL), stirred at 15° C. for 30 minutes, then added with sodium cyanoborohydride (23.44 mg, 372.99 μmol), and stirred at 15° C. for 1 hour. LCMS showed the reaction was complete. The reaction solution was evaporated to dryness under reduced pressure, and the obtained crude product was purified by preparative chromatography (chromatographic column: Waters Xbridge C18 150×30 mm×5 μm; mobile phase: 10 mM ammonium bicarbonate solution as mobile phase A, acetonitrile as mobile phase B, B %: 16%-46%, gradient time: 11.5 min) to obtain compound 10. $^1$H NMR (400 MHz, $CD_3OD$): δ 7.99 (s, 1H), 5.28 (br t, J=8.4 Hz, 1H), 4.36-4.28 (m, 1H), 4.20 (t, J=9.4 Hz, 2H), 4.03 (dd, J=6.5, 10.5 Hz, 2H), 3.97-3.90 (m, 1H), 3.80-3.74 (m, 2H), 3.11-3.03 (m, 2H), 2.78-2.70 (m, 5H), 2.66-2.60 (m, 2H), 2.53-2.42 (m, 1H), 2.24-2.04 (m, 4H), 1.95-1.85 (m, 2H), 1.79-1.72 (m, 1H), 1.63-1.52 (m, 2H), 1.18 (s, 3H); LCMS (ESI): m/z: 479.3 (M+1).

Example 11: Compound 11, Compound 11A and Compound 11B

11

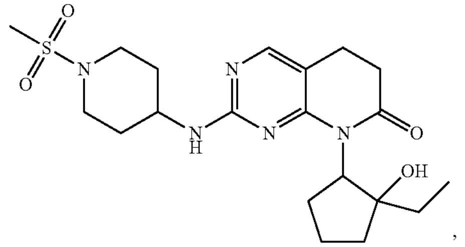

, 11A or 11B

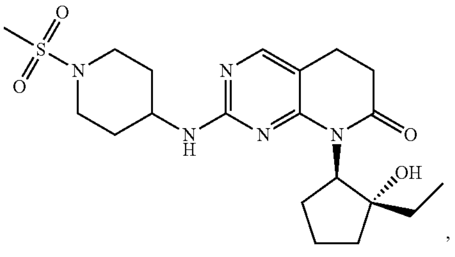

, 11B or 11A

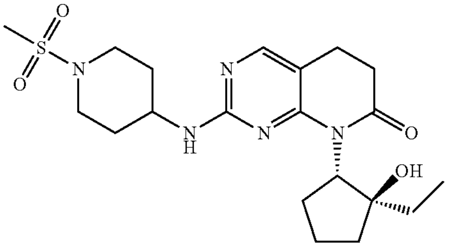

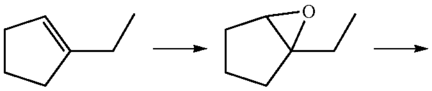

11-a 11-b

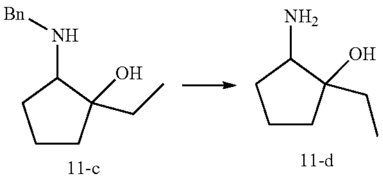

11-c 11-d

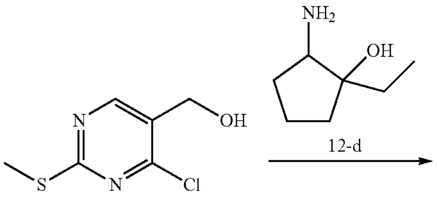

11-e

-continued

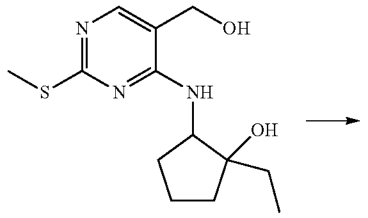

11-f

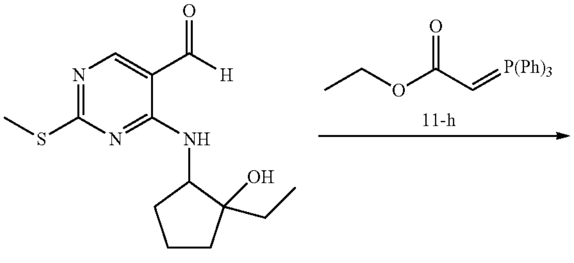

11-g

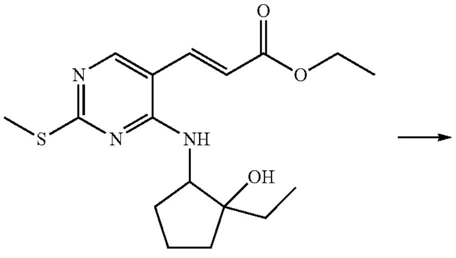

11-i

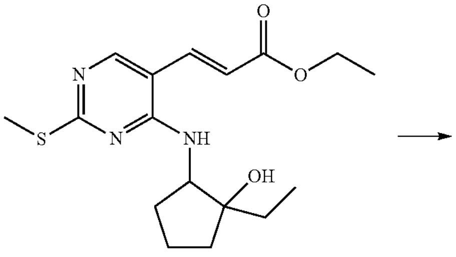

11-j

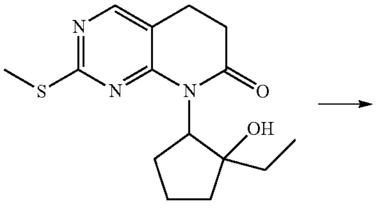

11-k

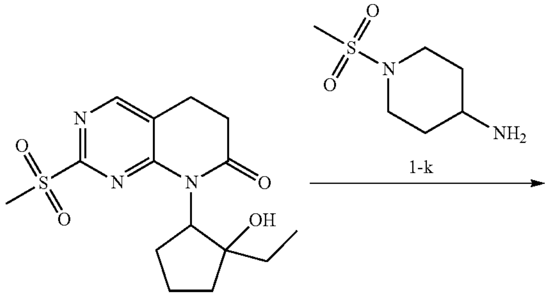

11-l

-continued

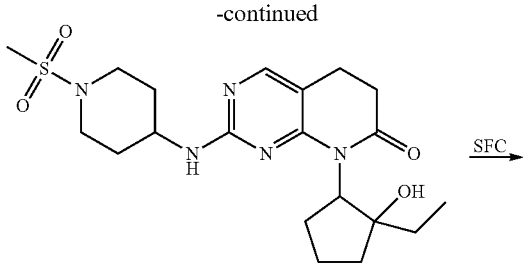

11

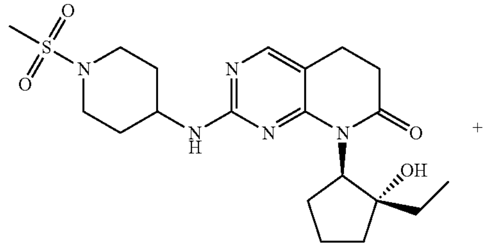

11A or 11B

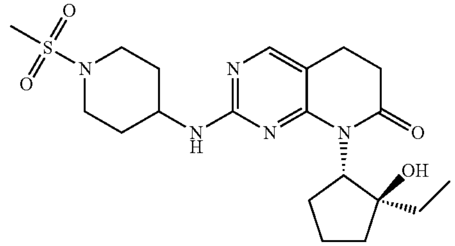

11B or 11A

Synthesis of Compound 11-b

Compound 11-a (4.2 g, 43.67 mmol) was added to dichloromethane (150 mL), cooled to 0° C., then m-chloroperoxybenzoic acid (13.30 g, 65.51 mmol, 85% purity) was slowly added in batches, the reaction solution was reacted at 15° C. for 16 hours. The mixture was filtered and the filtrate was quenched with saturated sodium sulfite solution (50 mL). The separated aqueous phase was extracted with dichloromethane (20 mL×2), the organic phases were combined, washed with saturated sodium bicarbonate solution (50 mL×2) and saturated brine (50 mL), dried over anhydrous sodium sulfate, and filtered, the filtrate was evaporated to dryness at no higher than 15° C. under reduced pressure to obtain compound 11-b. $^{1}H$ NMR (400 MHz, $CDCl_3$): δ 2.07-1.32 (m, 9H), 0.98 (t, J=7.5 Hz, 3H).

Synthesis of Compound 11-c

Compound 11-b (5.1 g, 45.47 mmol) was added to water (50 mL), followed by benzylamine (4.38 g, 40.92 mmol, 4.46 mL), and the reaction solution was stirred at 100° C. for 16 hours. LCMS showed the reaction was complete. The reaction solution was cooled with ice water, the pH was adjusted to 1 with concentrated hydrochloric acid, and extracted with ethyl acetate (30 mL×2). The pH of the aqueous phase was adjusted to 10 with 5 M sodium hydroxide, extracted with ethyl acetate (30 mL×3), the organic phases were combined and washed with saturated brine (30 mL×2), dried over anhydrous sodium sulfate, filtered, and evaporated to dryness. The obtained crude product was purified by silica gel column chromatography (petroleum ether/ethyl acetate=1/1) to obtain compound 11-c. $^1$H NMR (400 MHz, $CDCl_3$): δ 7.19-7.15 (m, 1H), 7.30-7.11 (m, 4H), 3.83-3.62 (m, 2H), 2.81 (t, J=6.6 Hz, 1H), 1.79-1.43 (m, 8H), 0.93-0.86 (m, 3H); LCMS (ESI): m/z: 220.2 (M+1).

Synthesis of Compound 11-d

Compound 11-c (2.6 g, 11.85 mmol) was added to isopropanol (30 mL), and wet palladium hydroxide/carbon (0.5 g, 50%) was added under nitrogen protection. The reaction system was purged with hydrogen several times, and the reaction was stirred at 25° C. for 16 hours under hydrogen (50 psi). TLC (dichloromethane:methanol=10:1) showed that the reaction was complete. The reaction solution was filtered through diatomite, and the filtrate was evaporated to dryness to obtain compound 11-d. $^1$H NMR (400 MHz, $CDCl_3$): δ 3.10 (dd, J=5.2, 6.3 Hz, 1H), 2.17 (ddd, J=2.6, 6.6, 13.1 Hz, 1H), 1.79-1.72 (m, 3H), 1.61-1.50 (m, 3H), 1.41-1.30 (m, 1H), 1.03-0.99 (m, 3H).

Synthesis of Compound 11-f

Compound 11-e (2.3 g, 12.06 mmol) and compound 12-d (1.56 g, 12.06 mmol) were added to acetonitrile (30 mL), followed by triethylamine (1.83 g, 18.10 mmol, 2.52 mL), and the reaction solution was stirred at 80° C. for 16 hours. LCMS showed the reaction was complete. The reaction solution was cooled to 25° C., concentrated under reduced pressure to remove acetonitrile, and the obtained crude product was purified by silica gel column chromatography (petroleum ether/ethyl acetate=1/1) to obtain compound 11-f. $^1$H NMR (400 MHz, $CDCl_3$): δ 7.78 (s, 1H), 4.53 (t, J=6.7 Hz, 1H), 4.49 (s, 2H), 2.53 (s, 3H), 2.37-2.27 (m, 1H), 1.87-1.49 (m, 8H), 0.96 (t, J=7.4 Hz, 3H); LCMS (ESI): m/z: 284.2 (M+1).

Synthesis of Compound 11-g

Compound 11-f (2.38 g, 8.40 mmol) was added to ethyl acetate (40 mL), then manganese dioxide (7.30 g, 83.98 mmol) was added, and the mixture was reacted at 60° C. for 2 hours. TLC (petroleum ether/ethyl acetate=1/1) showed that the reaction was complete. The reaction solution was cooled to 25° C. and filtered, the filter cake was washed with methanol (20 mL×3), and the filtrate was evaporated to dryness to obtain compound 11-g. $^1$H NMR (400 MHz, $CDCl_3$): δ 9.73 (s, 1H), 8.66 (br d, J=4.8 Hz, 1H), 8.35 (s, 1H), 4.47 (td, J=7.6, 8.7 Hz, 1H), 2.58 (s, 3H), 2.34-2.26 (m, 1H), 1.95-1.70 (m, 5H), 1.66-1.60 (m, 1H), 1.41 (q, J=7.3 Hz, 2H), 0.96 (t, J=7.3 Hz, 3H).

Synthesis of Compound 11-i

Compound 11-g (2.3 g, 8.17 mmol) was added to dichloromethane (50 mL), then compound 11-h (2.99 g, 8.58 mmol) was added, and the reaction solution was stirred at 20° C. for 2 hours. TLC (petroleum ether/ethyl acetate=5/1) showed that the reaction was complete and new compounds were formed. The reaction solution was evaporated to dryness under reduced pressure, and the obtained crude product was purified by silica gel column chromatography (petroleum ether/ethyl acetate=5/1) to obtain compound 11-i. $^1$H NMR (400 MHz, $CDCl_3$): δ 8.11 (s, 1H), 7.42 (d, J=15.8 Hz, 1H), 6.22 (d, J=15.8 Hz, 1H), 4.95 (br d, J=5.5 Hz, 1H), 4.29 (ddd, J=6.0, 7.8, 10.5 Hz, 2H), 4.21 (q, J=7.1 Hz, 2H), 2.46 (s, 3H), 2.22-2.10 (m, 1H), 1.84-1.71 (m, 3H), 1.70-1.59 (m, 1H), 1.53-1.42 (m, 1H), 1.27 (t, J=7.2 Hz, 3H), 0.88 (t, J=7.3 Hz, 3H).

Synthesis of Compound 11-j

Compound 11-i (2.7 g, 7.68 mmol) was added to 2-methyltetrahydrofuran (50 mL), then $Rh(PPh_3)_3Cl$ (710.77 mg, 768.22 μmol) was added, the reaction solution was purged with hydrogen several times, and stirred at 80° C. for 20 hours under hydrogen (15 Psi). TLC (petroleum ether/ethyl acetate=3/1) showed that the reaction was complete and new compound was formed. The reaction solution was evaporated to dryness under reduced pressure, and the obtained crude product was purified by silica gel column chromatography (petroleum ether/ethyl acetate=3/1) to obtain compound 11-j. $^1$H NMR (400 MHz, $CDCl_3$): δ 7.73 (s, 1H), 5.66 (br d, J=5.3 Hz, 1H), 4.21 (ddd, J=5.8, 7.9, 10.4 Hz, 1H), 4.10-4.04 (m, 3H), 2.64-2.60 (m, 2H), 2.53-2.48 (m, 2H), 2.42 (s, 3H), 2.14-2.07 (m, 1H), 1.84-1.71 (m, 3H), 1.62-1.48 (m, 3H), 1.20-1.18 (m, 3H), 0.88-0.85 (m, 3H).

Synthesis of Compound 11-k

Compound 11-j (600 mg, 1.70 mmol) was added to N-methylpyrrolidone (10 mL), followed by DBU (516.82 mg, 3.39 mmol, 511.70 μL), and the reaction solution was stirred at 80° C. for 16 hours. LCMS showed the reaction was complete. The reaction solution was cooled to 25° C., added with water (10 mL), and extracted with ethyl acetate (10 mL×3), the organic phases were combined, washed with saturated brine (20 mL×2), dried over anhydrous sodium sulfate, and filtered, the filtrate was evaporated to dryness, and the obtained crude product was purified by silica gel column chromatography (petroleum ether/ethyl acetate=1/1) to obtain compound 11-k. $^1$H NMR (400 MHz, $CDCl_3$): δ 8.13 (s, 1H), 4.96 (br t, J=8.9 Hz, 1H), 2.77-2.71 (m, 2H), 2.64-2.60 (m, 2H), 2.48 (s, 3H), 1.96-1.73 (m, 6H), 1.48-1.41 (m, 1H), 1.22-1.18 (m, 2H), 0.84 (t, J=7.4 Hz, 3H); LCMS (ESI): m/z: 308.1 (M+1).

Synthesis of Compound 11-1

Compound 11-k (200 mg, 650.60 μmol) was added to 2-methyltetrahydrofuran (5 mL) and water (1 mL), then potassium hydrogen persulfate (999.91 mg, 1.63 mmol) was added, and the reaction solution was stirred at 25° C. for 2 hours. LCMS showed the reaction was complete. The reaction solution was quenched with saturated sodium sulfite solution (20 mL), and extracted with ethyl acetate (20 mL×3), the organic phases were combined, washed with saturated brine (20 mL), dried over anhydrous sodium sulfate, and filtered, and the filtrate was evaporated to dryness to obtain compound 11-1. $^1$H NMR (400 MHz, $CDCl_3$): δ 8.54 (s, 1H), 5.11 (br t, J=7.4 Hz, 1H), 3.33 (s, 3H), 3.06-2.99 (m, 2H), 2.87-2.78 (m, 2H), 2.05-1.81 (m, 6H), 1.30-1.23 (m, 2H), 0.94 (t, J=7.4 Hz, 3H); LCMS (ESI): m/z: 322.1 (M+1-18).

Synthesis of Compound 11

Compound 11-1 (390 mg, 1.15 mmol) and compound 1-k (1.23 g, 5.75 mmol, hydrochloride) were added to N-methylpyrrolidone (10 mL), followed by diisopropylethylamine (1.04 g, 8.04 mmol, 1.40 mL), the reaction solution was stirred at 140° C. for 16 hours. LCMS showed the reaction was complete. The reaction solution was cooled to 20° C., added with water (10 mL), and extracted with ethyl acetate (15 mL×3), the organic phases were combined, washed with saturated brine (20 mL), dried over anhydrous sodium sulfate, and filtered, the filtrate was evaporated to dryness, and the obtained crude product was purified by preparative chromatography (chromatographic column: Waters Xbridge C18 150×50 mm×10 μm; mobile phase: 0.05% aqueous ammonia solution as mobile phase A, acetonitrile as mobile phase B, B %: 18%-48%, gradient time: 11.5 min) to obtain compound 11. $^1$H NMR (400 MHz, $CD_3OD$): δ 7.99 (s, 1H), 5.31 (br t, J=8.4 Hz, 1H), 3.96-3.86 (m, 1H), 3.72 (br dd, J=3.4, 11.9 Hz, 2H), 2.97 (dt, J=2.3, 11.6 Hz, 2H), 2.88 (s, 3H), 2.77-2.70 (m, 2H), 2.65-2.59 (m, 2H), 2.49-2.38 (m, 1H), 2.15-2.05 (m, 5H), 1.96-1.85 (m, 2H), 1.77 (dd, J=6.1, 12.0 Hz, 1H), 1.68-1.57 (m, 2H), 1.52-1.41 (m, 2H), 0.91 (t, J=7.4 Hz, 3H); LCMS (ESI): m/z: 438.3 (M+1).

Resolution of Compound 11

Compound 11 was chiral separated by SFC to obtain 11A and 11B.

Compound 11 was prepared by SFC (column: polyoxymethylene-coated chiral stationary phase (250 mm×30 mm×10 μm); mobile phase: 65% [0.1% ammonia ethanol solution]; purified to obtain compound 11A (retention time 0.479 minutes) and compound 11B (retention time 1.516 minutes).

Compound 11A: $^1$H NMR (400 MHz, $CD_3OD$): δ 7.87 (s, 1H), 5.19 (br t, J=8.4 Hz, 1H), 3.84-3.76 (m, 1H), 3.60 (br dd, J=3.5, 11.9 Hz, 2H), 2.85 (dt, J=2.4, 11.6 Hz, 2H), 2.76 (s, 3H), 2.64-2.57 (m, 2H), 2.52-2.46 (m, 2H), 2.37-2.26 (m, 1H), 2.05-1.95 (m, 4H), 1.86-1.73 (m, 2H), 1.65 (dd, J=6.0, 12.1 Hz, 1H), 1.55-1.45 (m, 2H), 1.40-1.30 (m, 2H), 0.79 (t, J=7.4 Hz, 3H); LCMS (ESI): m/z: 438.3 (M+1).

Compound 11B: $^1$H NMR (400 MHz, $CD_3OD$): δ 7.87 (s, 1H), 5.19 (br t, J=8.4 Hz, 1H), 3.84-3.75 (m, 1H), 3.64-3.56 (m, 2H), 2.85 (dt, J=2.5, 11.6 Hz, 2H), 2.76 (s, 3H), 2.66-2.56 (m, 2H), 2.53-2.46 (m, 2H), 2.38-2.26 (m, 1H), 2.06-1.93 (m, 4H), 1.86-1.72 (m, 2H), 1.65 (dd, J=6.2, 11.9 Hz, 1H), 1.57-1.44 (m, 2H), 1.39-1.28 (m, 2H), 0.79 (t, J=7.4 Hz, 3H); LCMS (ESI): m/z: 438.3 (M+1).

Activity Test

Experimental Example 1: Enzyme Activity Test

CDK2/CyclinA2 Kinase Activity Test

Experimental materials: CDK2/CyclinA2 kinase detection kit was purchased from Promega. Nivo Multilabel Analyzer (PerkinElmer).

Experimental method: Kinase buffer dilution enzyme in the kit, substrate, adenosine triphosphate and inhibitor were used. The compounds to be tested were diluted 5-fold to the 8th concentration with a row gun, that is, from 50 μM to 0.65 nM, the concentration of DMSO was 5%, and a double-replicate well experiment was set up. 1 μL of each concentration gradient of inhibitor, 2 μL of CDK2/CyclinA2 enzyme (1.6 ng), and 2 μL of a mixture of substrate and ATP (50 μM of adenosine triphosphate, 0.1 μg/μL of substrate) were added to the microplate, and at this time, the final concentration gradient of compound was diluted from 10 μM to 0.13 nM. The reaction system was placed at 25° C. and reacted for 60 minutes. After the reaction was complete, 5 μL of ADP-Glo reagent was added to each well, and the reaction was continued at 25° C. for 40 minutes. At the end of the reaction, 10 μL of kinase detection reagent was added to each well. After the reaction was continued at 25° C. for 30 minutes, the chemiluminescence was read by a multi-label analyzer with an integration time of 0.5 seconds.

CDK2/CyclinE1 Kinase Activity Test

Experimental materials: CDK2/CyclinE1 kinase detection kit was purchased from Promega. Nivo Multilabel Analyzer (PerkinElmer).

Experimental method: Kinase buffer dilution enzyme in the kit, substrate, adenosine triphosphate and inhibitor were used. The compounds to be tested were diluted 5-fold to the 8th concentration with a row gun, that is, from 50 μM to 0.65 nM, the concentration of DMSO was 5%, and a double-replicate well experiment was set up. 1 μL of each concentration gradient of inhibitor, 2 μL of CDK2/CyclinE1 enzyme (2 ng), and 2 μL of a mixture of substrate and ATP (150 μM of adenosine triphosphate, 0.1 μg/μL of substrate) were added to the microplate, and at this time, the final concentration gradient of compound was diluted from 10 μM to 0.13 nM. The reaction system was placed at 25° C. and reacted for 60 minutes. After the reaction was complete, 5 μL of ADP-Glo reagent was added to each well, and the reaction was continued at 25° C. for 40 minutes. At the end of the reaction, 10 μL of kinase detection reagent was added to each well. After the reaction was continued at 25° C. for 30 minutes, the chemiluminescence was read by a multi-label analyzer with an integration time of 0.5 seconds.

CDK4/CyclinD1 Kinase Activity Test

Experimental materials: CDK4/CyclinD1 kinase was purchased from Invitrogen, reaction substrate LANCE Ultra ULight™-4E-BP-1 (Thr37146) Peptide and EU-ANTI-P-4EBP1 (THR37/46) were purchased from PerkinElmer. Nivo Multilabel Analyzer (PerkinElmer).

Experimental method: preparation of kinase buffer: The components of the buffer include: 50 mM of hydroxyethylpiperazine ethanethiosulfonic acid solution with pH 7.5, 1 mM of EDTA, 10 mM of magnesium chloride, 0.01% lauryl polyoxyethylene ether (Brij-35), 2 mM of enzyme dithiothreitol, kinase buffer dilution enzyme, substrate LANCE Ultra ULight™-4E-BP-1 (Thr37146) Peptide, adenosine triphosphate and inhibitor. The compounds to be tested were diluted 5-fold to the 8th concentration with a row gun, that is, from 40 μM to 0.512 nM, the concentration of DMSO was 4%, and a double-replicate well experiment was set up. 2.5 μL of each concentration gradient of inhibitor and 5 μL of CDK4/CyclinD1 enzyme (0.5 ng) were added to the microplate, the reaction was placed at 25° C. and reacted for 60 min, then 2.5 μL of a mixture of substrate and ATP (350 μM of adenosine triphosphate, 12.5 nM of substrate) was added, at this time, the final concentration gradient of compound was diluted from 10 μM to 0.128 nM. The reaction system was continued at 25° C. for 120 minutes. After the reaction was complete, a mixture of 5 μL of EDTA and 2× LANCE™ Detection Buffer (1:1) was added to each well, and reacted at 25° C. for 5 minutes, after the reaction was complete, 5 μL of LANCE Ultra Eu-anti-P-4E-BP1 (Thr37MS) (4 nM) was added to each well, and reacted at 25° C. for 60 minutes, the reaction signal was detected by Nivo instrument according to the principle of time-resolved fluorescence resonance energy transfer.

CDK6/CyclinD1 Kinase Activity Test

Experimental materials: CDK6/CyclinD1 kinase was purchased from Carna, reaction substrate LANCE Ultra ULight™-4E-BP-1 (Thr37146) Peptide and EU-ANTI-P-4EBP1 (THR37/46) were purchased from PerkinElmer. Nivo Multilabel Analyzer (PerkinElmer).

Experimental method: preparation of kinase buffer: The components of the buffer include: 50 mM of hydroxyethylpiperazine ethanethiosulfonic acid solution with pH 7.5, 1 mM of EDTA, 10 mM of magnesium chloride, 0.01% lauryl polyoxyethylene ether (Brij-35), 2 mM of enzyme dithiothreitol, kinase buffer dilution enzyme, substrate LANCE Ultra ULight™-4E-BP-1 (Thr37146) Peptide, adenosine triphosphate and inhibitor. The compounds to be tested were diluted 5-fold to the 8th concentration with a row gun, that is, from 40 μM to 0.512 nM, the concentration of DMSO was 4%, and a double-replicate well experiment was set up. 2.5 μL of each concentration gradient of inhibitor and 5 μL of CDK6/CyclinD1 enzyme (0.5 ng) were added to the microplate, the reaction was placed at 25° C. and reacted for 60 min, then 2.5 μL of a mixture of substrate and ATP (250 μM adenosine triphosphate, 12.5 nM substrate) was added, at this time, the final concentration gradient of compound was diluted from 10 μM to 0.128 nM. The reaction system was continued at 25° C. for 120 minutes. After the reaction was complete, a mixture of 5 μL of EDTA and 2× LANCE™ Detection Buffer (1:1) was added to each well, and reacted at 25° C. for 5 minutes, after the reaction was complete, 5 μL of LANCE Ultra Eu-anti-P-4E-BP1(Thr37MS) (4 nM) was added to each well, and reacted at 25° C. for 60 minutes, the reaction signal was detected by Nivo instrument according to the principle of time-resolved fluorescence resonance energy transfer.

CDK9/CyclinT1 Kinase Activity Assay

Experimental materials: CDK9/CyclinT1 kinase was purchased from Carna, the ADP-Glo detection kit was purchased from Promega, the PKDTide substrate and kinase reaction buffer were purchased from Signalchem. Nivo Multilabel Analyzer (PerkinElmer).

Experimental method: Kinase buffer dilution enzyme in the kit, substrate, adenosine triphosphate and inhibitor were used. The compounds to be tested were diluted 5-fold to the 8th concentration with a row gun, that is, from 50 μM to 0.65 nM, the concentration of DMSO was 5%, and a double-replicate well experiment was set up. 1 μL of each concentration gradient of inhibitor, 2 μL of CDK9/CyclinT1 enzyme (4 ng), and 2 μL of a mixture of substrate and ATP (100 μM adenosine triphosphate, 0.2 μg/μL substrate) were added to the microplate, and at this time, the final concentration gradient of compound was diluted from 10 μM to 0.13 nM. The reaction system was placed at 25° C. and reacted for 60 minutes. After the reaction was complete, 5 μL of ADP-Glo reagent was added to each well, and the reaction was continued at 25° C. for 40 minutes. At the end of the reaction, 10 μL of kinase detection reagent was added to each well. After the reaction was continued at 25° C. for 30 minutes, the chemiluminescence was read by a multi-label analyzer with an integration time of 0.5 seconds.

Data Analysis

Using the equation (Sample−Min)/(Max−Min)×100% to convert the original data into inhibition rate, the $IC_{50}$ value can be obtained by curve fitting with four parameters (obtained by the mode of log(inhibitor) vs. response—Variable slope in GraphPad Prism). Table 1 provides the enzymatic inhibitory activities of the compounds of the present invention on CDK2/CyclinA2, CDK2/CyclinE1, CDK4/CyclinD1, CDK6/CyclinD1, CDK9/CyclinT1.

TABLE 1

Enzyme activity data ($IC_{50}$) of the compounds of the Examples of the present invention

| Compound NO. | CDK2/ cyclinA (nM) | CDK2/ CyclinE1 (nM) | CDK4/ cyclinD1 (nM) | CDK6/ cyclinD1 (nM) | CDK9/ CyclinT1 (nM) |
|---|---|---|---|---|---|
| PF-06873600 | 0.54 | 2.03 | 1.85 | 0.47 | 17.21 |
| Compound 1A | 0.28 | 1.19 | 5.9 | 1.5 | 110 |
| Compound 3 | 1.18 | — | 23.58 | 4.74 | — |
| Compound 4 | 1.32 | — | 37.54 | 5.42 | — |
| Compound 5 | 1.74 | — | 46.94 | 8.95 | — |
| Compound 6 | 1.13 | — | 38.11 | 5.26 | — |
| Compound 7 | 1.40 | — | 3.99 | 1.52 | — |
| Compound 8 | 1.78 | — | 14.90 | 3.40 | — |
| Compound 9 | 1.40 | — | 15.70 | 3.69 | — |
| Compound 10 | 1.52 | — | 9.09 | 2.65 | — |

Experimental conclusion: The compounds of the present invention have significant inhibitory activities on CDK2, CDK4 and CDK6 kinases, and have high selectivity to CDK9.

Experimental Example 2: Cell Experiment

HCT116 Cell Activity Test

Experimental materials: McCoy' 5a medium, fetal bovine serum, and penicillin/streptomycin antibiotics were purchased from Vicente. CellTiter-Glo (chemiluminescence detection reagent for cell viability) reagent was purchased from Promega. The HCT116 cell line was purchased from Cobioer Biosciences Co., Ltd. Nivo Multilabel Analyzer (PerkinElmer).

Experimental method: HCT116 cells were seeded in a white 96-well plate, 80 μL of cell suspension per well, which contained 1000 HCT116 cells. The cell plate was incubated overnight in a carbon dioxide incubator. The compounds to be tested were diluted 5-fold to the 9th concentration with a row gun, that is, from 2 mM to 5.12 nM, and a double-replicate well experiment was set up. 78 μL of medium was added to the middle plate, and then transferred 2 μL per well of the gradient diluted compound to the middle plate according to the corresponding position, mixed well and transferred 20 μL per well to the cell plate. The concentration of compound transferred to the cell plate ranged from 10 μM to 0.0256 nM. The cell plate was incubated in a carbon dioxide incubator for 4 days. Another cell plate was prepared, and the signal value was read as the maximum value (Max value in the equation below) on the day of drug addition to participate in data analysis. 25 μL of chemiluminescence detection reagent for cell viability was added to each well of the cell plate, and incubated at room temperature for 10 minutes to stabilize the luminescence signal. A multi-label analyzer was used for reading.

HCC1806 Cell Activity Test

Experimental materials: RPMI-1640 medium, fetal bovine serum, penicillin/streptomycin antibiotics were purchased from Vicente. CyQUANT Cell Proliferation Assays (Cell proliferation assay kit) reagents were purchased from ThermoFisher. The HCC1806 cell line was purchased from Cobioer Biosciences Co., Ltd. Nivo Multilabel Analyzer (PerkinElmer).

Experimental method: HCC1806 cells were seeded in a white 96-well plate, 80 μL of cell suspension per well, which contained 3000 HCC1806 cells. The cell plate was incubated overnight in a carbon dioxide incubator. The compounds to be tested were diluted 5-fold to the 9th concentration with a row gun, that is, from 10 mM to 25.6 nM, and a double-replicate well experiment was set up. 78 μL of medium was added to the middle plate, and then transferred 2 μL per well of the gradient diluted compound to the middle plate according to the corresponding position, mixed well and transferred 20 μL per well to the cell plate. The concentration of compound transferred to the cell plate ranged from 50 μM to 0.128 nM. The cell plate was incubated in a carbon dioxide incubator for 7 days. After reaching the incubation time, the cell supernatant was removed, and the cell plate was placed in a −80° C. refrigerator for 1 hour, after which 100 μL of Cyquant reagent was added to each well, and a multi-label analyzer was used for reading. Another cell plate was prepared, and the signal value was read as the maximum value (Max value in the equation below) on the day of drug addition to participate in data analysis.

MDA-MB-468 Cell Activity Test

Experimental materials: L15 medium, fetal bovine serum, penicillin/streptomycin antibiotics were purchased from Vicente. CellTiter-Glo (chemiluminescence detection reagent for cell viability) reagent was purchased from Promega. The MDA-MB-468 cell line was purchased from Cobioer Biosciences Co., Ltd. Nivo Multilabel Analyzer (PerkinElmer).

Experimental method: MDA-MB-468 cells were seeded in a white 96-well plate, 80 μL of cell suspension per well, which contained 1000 MDA-MB-468 cells. The cell plate was incubated overnight in a carbon dioxide incubator. The compounds to be tested were diluted 5-fold to the 9th concentration with a row gun, that is, from 10 mM to 25.6 nM, and a double-replicate well experiment was set up. 78 μL of medium was added to the middle plate, and then transferred 2 μL per well of the gradient diluted compound to the middle plate according to the corresponding position, mixed well and transferred 20 μL per well to the cell plate. The concentration of compound transferred to the cell plate ranged from 50 μM to 0.128 nM. The cell plate was incubated in a carbon dioxide incubator for 7 days. Another cell plate was prepared, and the signal value was read as the maximum value (Max value in the equation below) on the day of drug addition to participate in data analysis. 25 μL of chemiluminescence detection reagent for cell viability was added to each well of the cell plate, and incubated at room temperature for 10 minutes to stabilize the luminescence signal. A multi-label analyzer was used for reading.

Data analysis: Using the equation (Sample−Min)/(Max−Min)×100% to convert the original data into inhibition rate, the $IC_{50}$ value can be obtained by curve fitting with four parameters (obtained by the mode of log(inhibitor) vs. response—Variable slope in GraphPad Prism). Table 2 provides the inhibitory activity of the compounds of the present invention on cell proliferation.

TABLE 2

Antiproliferative activity (IC50) of the compounds of the Examples of the present invention on cells

| Compound NO. | HCT 116 (nM) | HCC1806 (nM) | MDA-MB-468 (nM) | Selectivity ratio(MDA-MB-468/HCC1806) |
|---|---|---|---|---|
| PF-06873600 | 140 | 457.5 | 120 | 0.26 |
| Compound 1A | 70 | 155.1 | 640 | 4.1 |

Experimental conclusion: The compounds of the present invention have significant inhibitory activities on the proliferation of HCT 116 and HCC1806 cells, and have poor activities on Rb-negative MDA-MB-468, and the selectivity is significantly better than PF-06873600.

Experimental Example 3: Pharmacokinetic Evaluation of the Compounds of the Present Invention

Experimental Animals

Healthy adult female Balb/c mice used in this study were purchased from Shanghai Lingchang Biotechnology Co., Ltd.

Formulation of Drug

Preparation of Dosing Solution for Intravenous Injection Group 1.11 mg of the compound to be tested was accurately weighed, 109.8 μL of DMSO was added and vortexed for 1 minute, 109.8 μL of solutol was added and vortexed for 1 minute to obtain a clear solution, then 878 μL of water was added and vortexed for 1 minute to obtain the final solution with a final concentration of 1 mg/mL, the dosing vehicle was 10% DMSO+10% solutol+80% water. The solution in the intravenous injection group was filtered with a 2 μm filter before administration.

Preparation of Dosing Solution for Oral Administration Group 1.61 mg of the compound to be tested was accurately weighed, 796 μL of 1% HPMC was added, sonicated at 45° C. for 20 minutes, and stirred for 15 minutes to obtain a homogeneous suspension solution with a final concentration of 2 mg/mL. The dosing vehicle was 1% HPMC.

Dosing 4 female Balb/c mice were divided into 2 groups according to 2 mice in each group. The first group was given 2 mg/kg of the compound to be tested by intravenous injection; the second group was given 10 mg/kg of the compound to be tested by gavage.

Sample Collection

The blood was collected from two animals at each time point by continuous blood collection. 30 μL of whole blood was collected before administration and at 0.0833, 0.25, 0.5, 1, 2 (only gavage group), 4, 6, 8 (only intravenous group), and 24 hours after administration, respectively. The whole blood was placed in an anticoagulant tube, centrifuged at 3200 g for 10 minutes at 4° C., the plasma was prepared and stored at −80° C. Drug concentration in the plasma was determined by LC/MS-MS.

TABLE 3

Pharmacokinetic results of the compounds of the Examples of the present invention

| | Pharmacokinetic Parameters | | | |
|---|---|---|---|---|
| | Intravenous Injection: 2 mg/kg | | Oral Administration: 10 mg/kg | |
| Compound | Half-Life $T_{1/2}$ (h) | Clearance Rate Cl (mL/Kg/min) | Oral Exposure $AUC_{0-t}$ (nM · h) | Oral Bioavailability F (%) |
| Compound 1A | 0.28 | 36.9 | 3372 | 31.4 |

Experimental conclusion: The compounds of the present invention have low clearance rate, high exposure, good oral bioavailability and excellent comprehensive pharmacokinetic properties in mice.

What is claimed is:

1. A compound represented by formula (I) or a pharmaceutically acceptable salt thereof, (I)

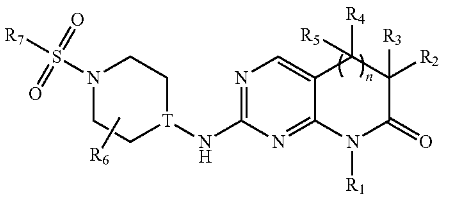

wherein,

T is N or CH;

$R_1$ is

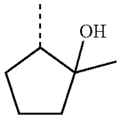
or
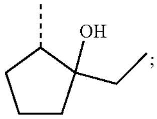
;

$R_2$ and $R_3$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_2$ and $R_3$ are joined together with the carbon atom to which they are attached form $C_{3-5}$ cycloalkyl, wherein the $C_{3-5}$ cycloalkyl is optionally substituted with 1, 2 or 3 $R^b$;

each $R^b$ is independently H, F, Cl, Br, I, —CN, —OH, $C_{1-3}$ alkoxy, $C_{1-3}$ alkyl or $C_{1-3}$ haloalkyl;

$R_4$ and $R_5$ are each independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

or $R_3$ and $R_4$ are joined together with the carbon atom to which they are attached form $C_{3-5}$ cycloalkyl, wherein the $C_{3-5}$ cycloalkyl is optionally substituted with 1, 2 or 3 $R^c$;

each $R^c$ is independently H, F, Cl, Br, I, —CN, —OH, $C_{1-3}$ alkoxy, $C_{1-3}$ alkyl or $C_{1-3}$ haloalkyl;

$R_6$ is H, F, Cl, Br, I, —CN, —OH, $C_{1-3}$ alkoxy, $C_{1-3}$ alkyl or $C_{1-3}$ haloalkyl;

$R_7$ is —$NH_2$, $C_{1-3}$ alkylamino, $C_{1-6}$ alkyl, $C_{3-5}$ cycloalkyl, 4- to 6-membered heterocycloalkyl, 5- to 6-membered heteroaryl or phenyl, wherein the $C_{1-6}$ alkyl, the $C_{3-5}$ cycloalkyl, the 4- to 6-membered heterocycloalkyl, the 5- to 6-membered heteroaryl and the phenyl are optionally substituted with 1, 2 or 3 $R^d$;

each $R^d$ is independently H, F, Cl, Br, I, —CN, —OH, $C_{1-3}$ alkoxy or $C_{1-3}$ alkyl, wherein the $C_{1-3}$ alkoxy and the $C_{1-3}$ alkyl are optionally substituted with 1, 2 or 3 substituents independently selected from F, Cl, Br, —CN, —OH and —$NH_2$;

n is 0, 1 or 2;

the 4- to 6-membered heterocycloalkyl and the 5- to 6-membered heteroaryl respectively comprise 1, 2, 3 or 4 heteroatoms independently selected from N, —O— and —S—.

2. The compound or the pharmaceutically acceptable salt thereof according to claim 1, each $R^b$ is independently H, F, Cl, Br, I, —CN, —OH, —$OCH_3$, —$CH_3$, —$CF_3$ or —$CH_2CH_3$;

or, each Re is independently H, F, Cl, Br, I, —CN, —OH, —$OCH_3$, —$CH_3$, —$CF_3$ or —$CH_2CH_3$;

or, each $R^d$ is independently H, F, Cl, Br, I, —CN, —OH, —$OCH_3$, —$CH_3$, —$CF_3$, —$CH_2CH_3$ or —$CH(CH_3)_2$;

or, $R_2$ and $R_3$ are joined together with the carbon atom to which they are attached form cyclopropyl, wherein the cyclopropyl is optionally substituted with 1, 2 or 3 $R^b$;

or, $R_3$ and $R_4$ are joined together with the carbon atom to which they are attached form cyclopropyl, wherein the cyclopropyl is optionally substituted with 1, 2 or 3 $R^c$.

3. The compound or the pharmaceutically acceptable salt thereof according to claim 1, wherein $R_2$ and $R_3$ are each independently H, F, Cl, Br, I, —CN, —OH, —$OCH_3$, —$CH_3$, —$CF_3$ or —$CH_2CH_3$;

or, $R_4$ and $R_5$ are each independently H, F, Cl, Br, I, —CN, —OH, —$OCH_3$, —$CH_3$, —$CF_3$ or —$CH_2CH_3$;

or, $R_6$ is H, F, Cl, Br, I, —CN, —OH, —$OCH_3$, —$CH_3$, or —$CH_2CH_3$.

4. The compound or the pharmaceutically acceptable salt thereof according to claim 1, wherein $R_7$ is —$NH_2$, —NH($CH_3$), —NH($CH_2CH_3$), —N$(CH_3)_2$, —$CH_3$, —$CH_2CH_3$, —$CH_2CH_2CH_3$, —$CH(CH_3)_2$, cyclopropyl, cyclopentyl, azacyclobutyl, pyrrolidinyl, tetrahydrofuranyl, piperidinyl, pyrazolyl, pyridyl or phenyl, wherein the —$CH_3$, the —$CH_2CH_3$, the —$CH_2CH_2CH_3$, the —$CH(CH_3)_2$, the cyclopropyl, the cyclopentyl, the azacyclobutyl, the pyrrolidinyl, the tetrahydrofuranyl, the piperidinyl, the pyrazolyl, the pyridyl or the phenyl are optionally substituted with 1, 2 or 3 $R^d$.

5. The compound or the pharmaceutically acceptable salt thereof according to claim 4, wherein $R_7$ is —$NH_2$, —NH($CH_3$), —NH($CH_2CH_3$), —N$(CH_3)_2$, —C$(R^d)_3$, —$CH_2CH_2R^d$,

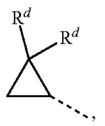
,
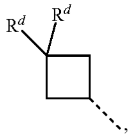
,
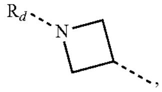
,

-continued
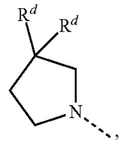, 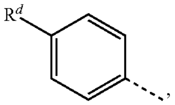, 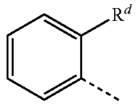 or
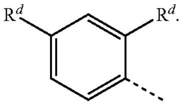
6. The compound or the pharmaceutically acceptable salt thereof according to claim 5, wherein $R_7$ is $-NH_2$, $-NH(CH_3)$, $-N(CH_3)_2$, $-CH_3$, $-CF_3$, $-CH_2CH_3$, $-CH(CH_3)_2$, $-CH_2CH_2OCH_3$,
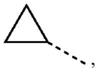, 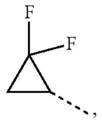, 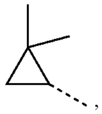, 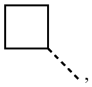, 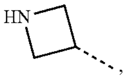, 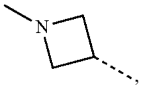, 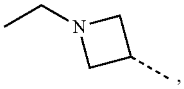, 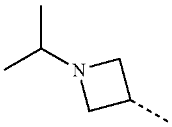, 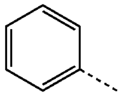, 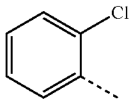 or
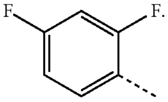
7. The compound or the pharmaceutically acceptable salt thereof according to claim 1, wherein the compound is
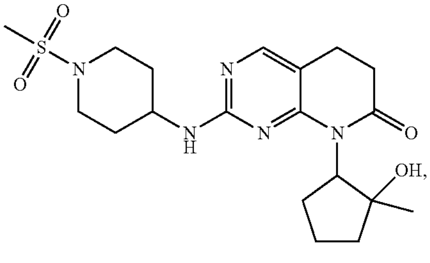
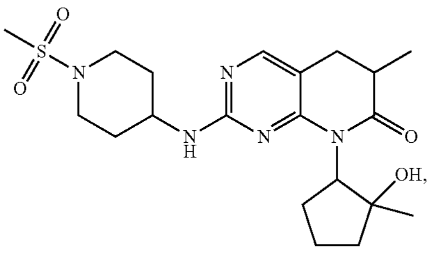
-continued
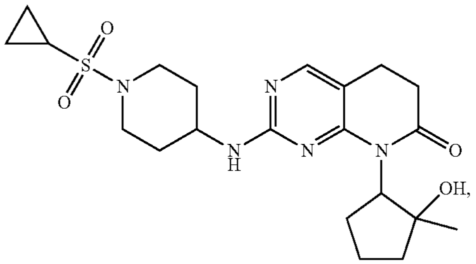
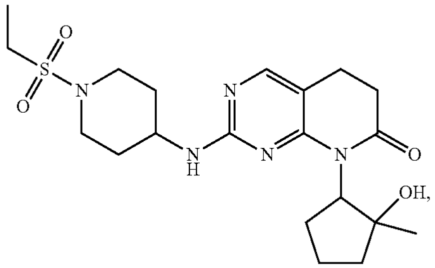
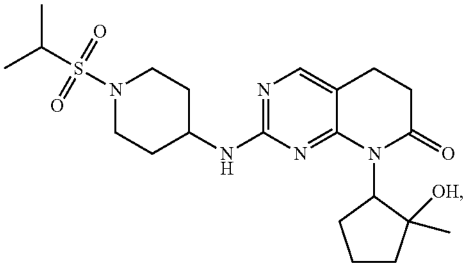
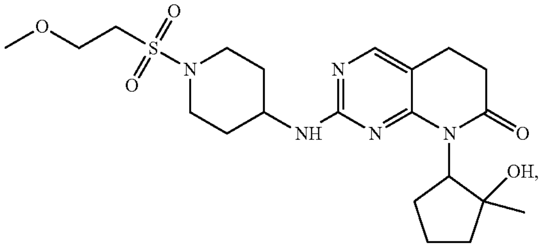
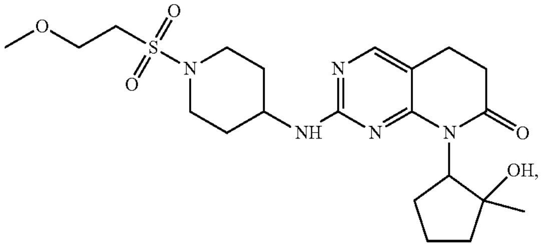
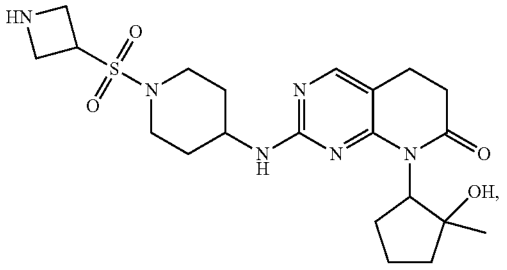

-continued
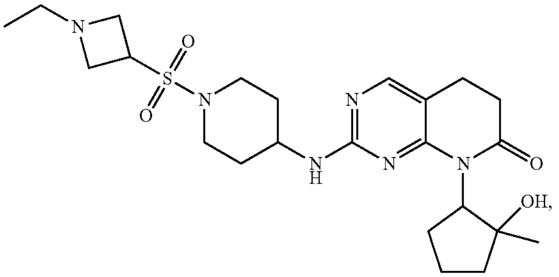
,
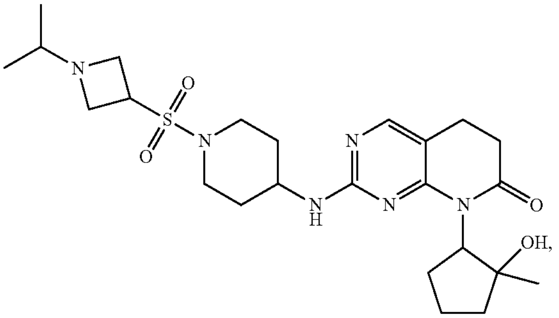
,
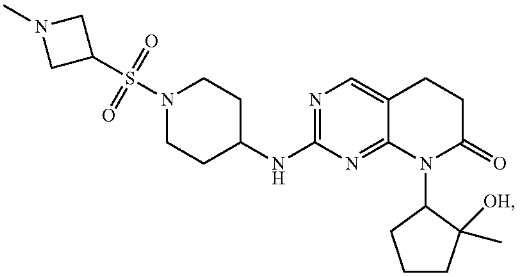
,
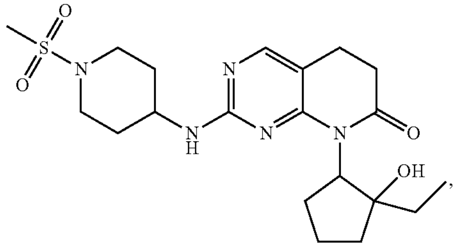
,
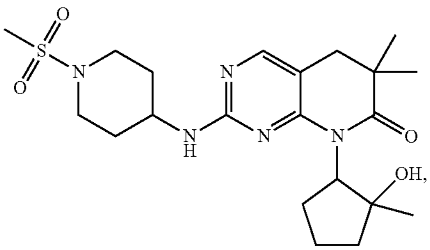
,
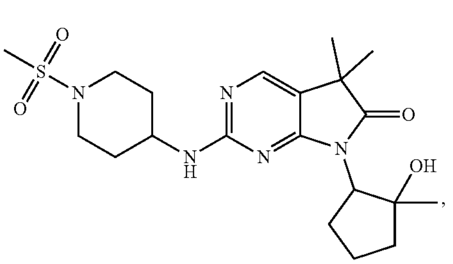
,
-continued
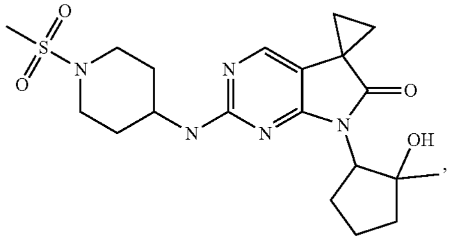
,
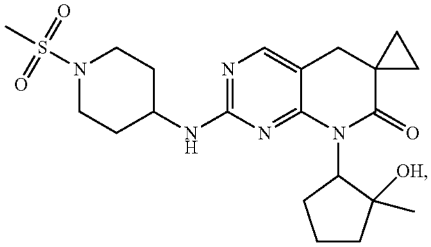
,
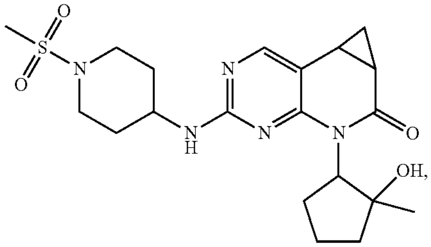
,
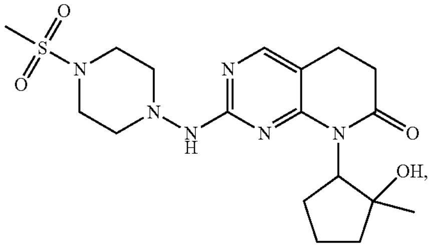
,
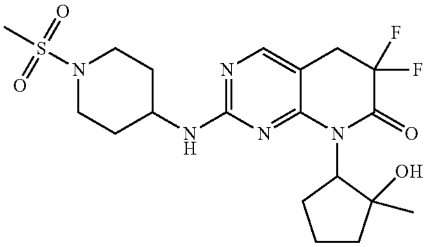
or
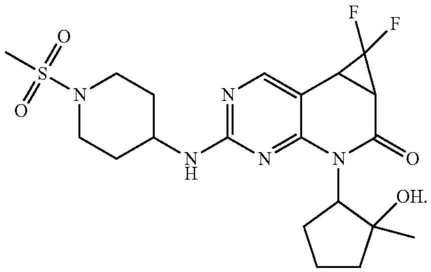
.
8. The compound or the pharmaceutically acceptable salt thereof according to claim 1, wherein the compound is:

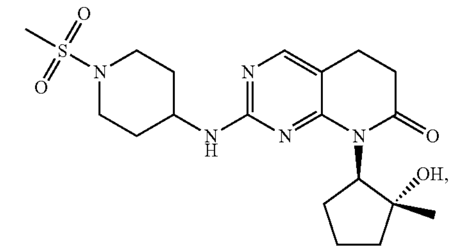
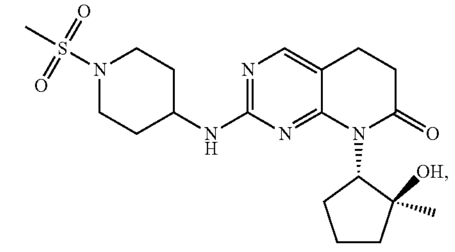
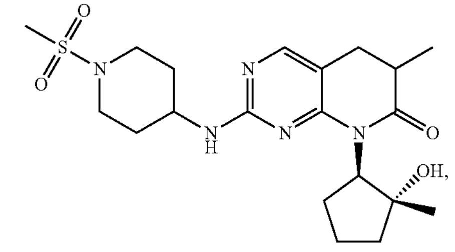
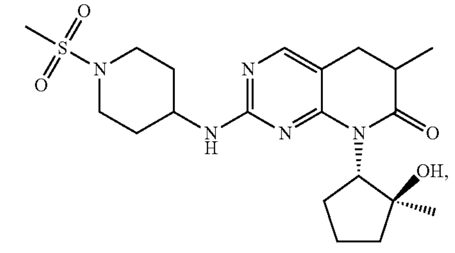
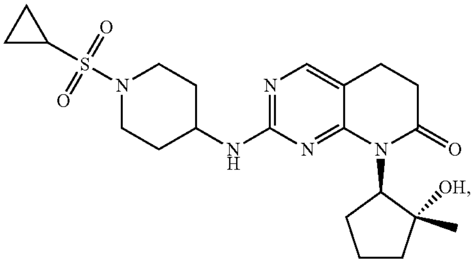
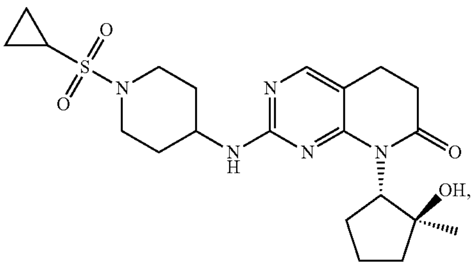
-continued
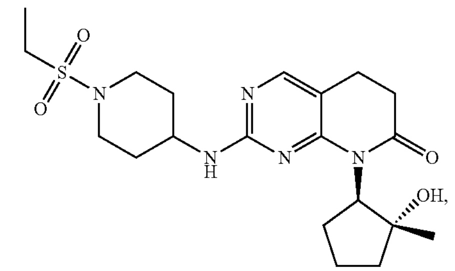
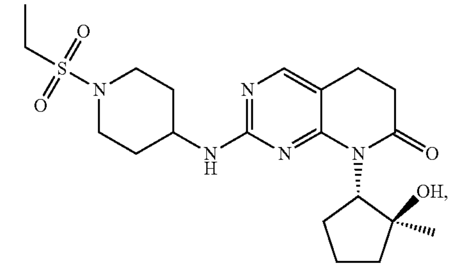
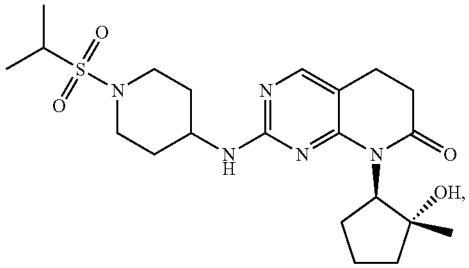
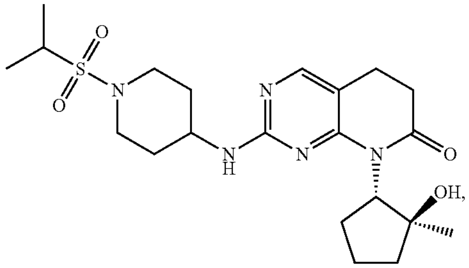
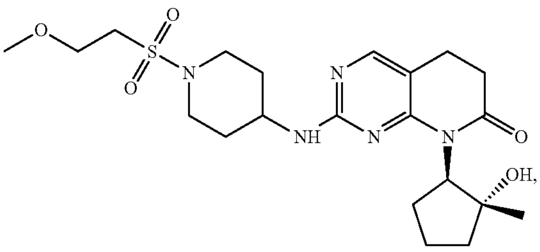
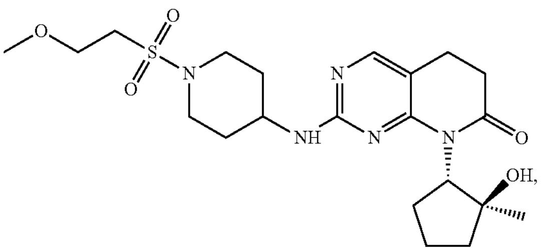

-continued
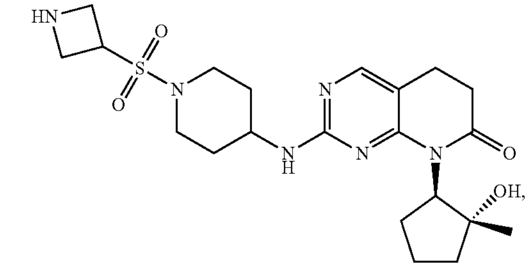
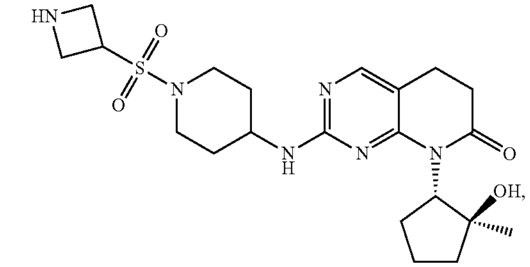
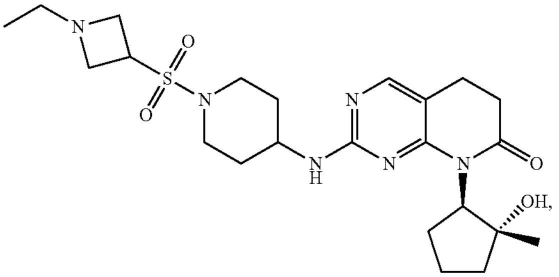
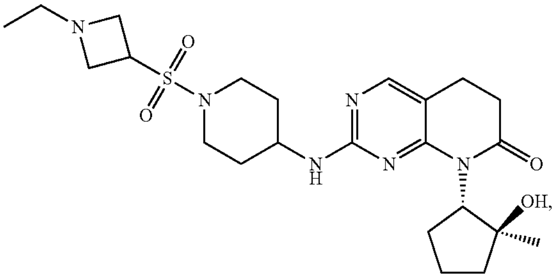
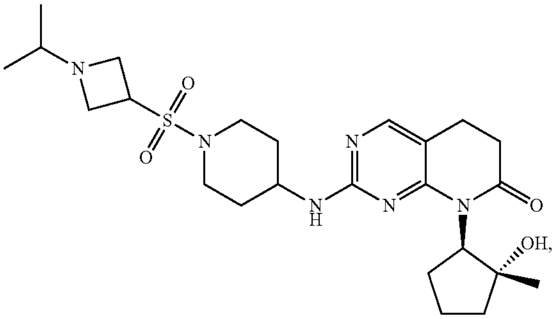
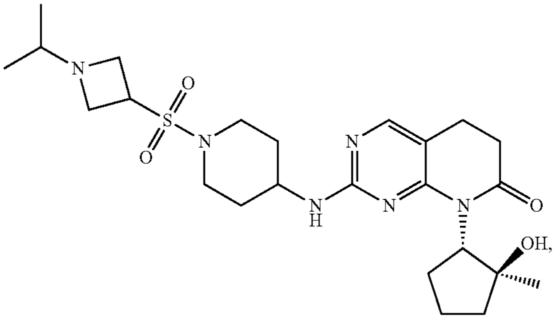
-continued
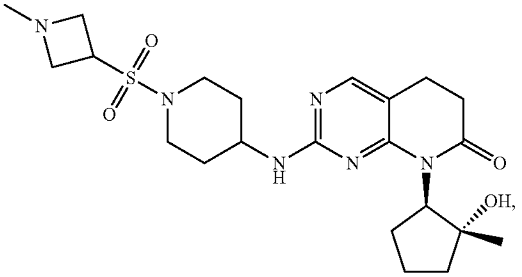
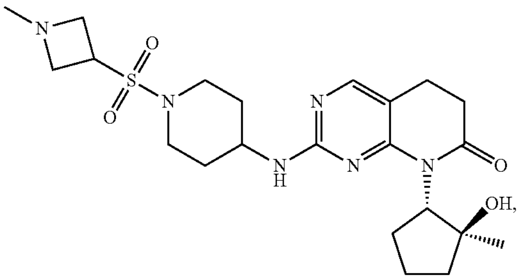
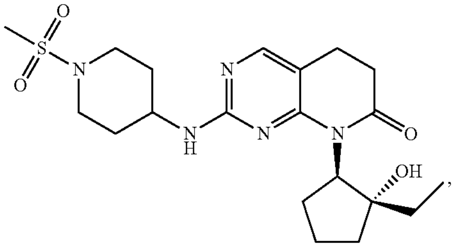
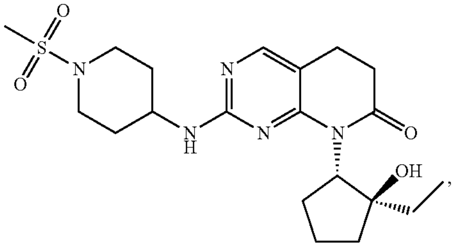
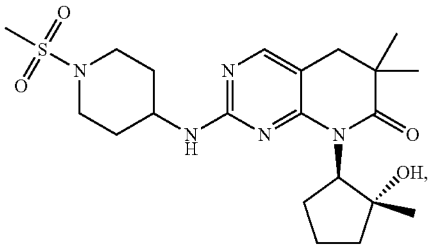
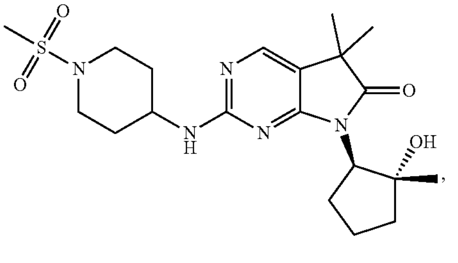

-continued

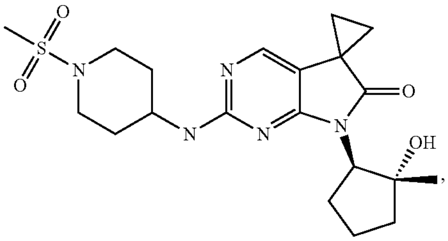

,

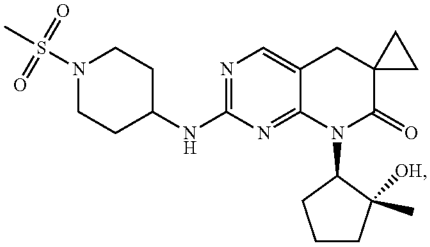

,

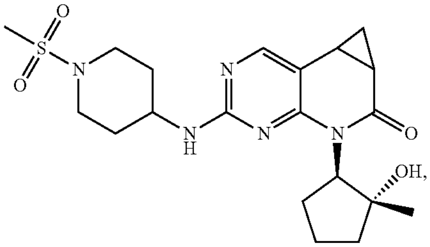

,

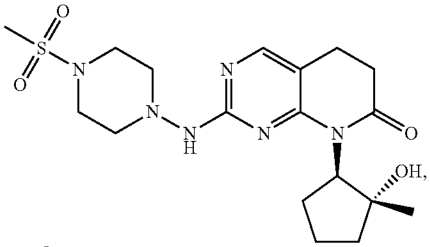

,

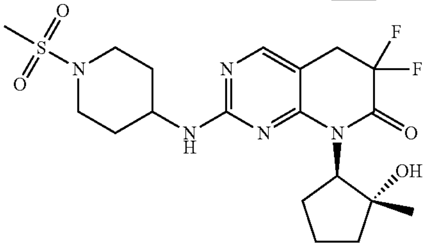

or

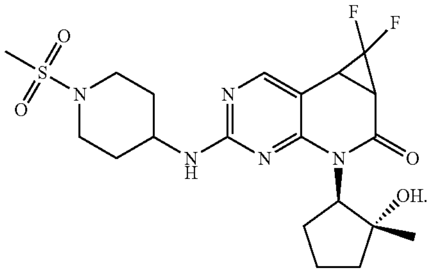

.

9. The compound or the pharmaceutically acceptable salt thereof according to claim 1, wherein the pharmaceutically acceptable salt is a hydrochloride salt.

10. A pharmaceutical composition, which comprises a therapeutically effective amount of the compound or the pharmaceutically acceptable salt thereof according to claim 1 and a pharmaceutically acceptable carrier.

11. A method for inhibiting CDK2/4/6 activity in a subject in need thereof, comprising administrating to the subject a medicament comprising the compound or the pharmaceutically acceptable salt thereof according to claim 1.

12. A method for treating solid tumor in a subject in need thereof, comprising administrating the compound or the pharmaceutically acceptable salt thereof according to claim 1 to a subject in need thereof.

13. The method according to claim 12, wherein the solid tumor is colorectal cancer or breast cancer.

14. A CDK4 inhibitor, wherein the CDK4 inhibitor is the compound or the pharmaceutically acceptable salt thereof according to claim 1.

15. A CDK6 inhibitor, wherein the CDK6 inhibitor is the compound or the pharmaceutically acceptable salt thereof according to claim 1.

16. A CDK2/4/6 triple inhibitor, wherein the CDK2/4/6 triple inhibitor is the compound or the pharmaceutically acceptable salt thereof according to claim 1.

* * * * *